(12) United States Patent
Mucha

(10) Patent No.: US 8,372,598 B2
(45) Date of Patent: Feb. 12, 2013

(54) SALT SELECTION OF MICROBIAL MUTANTS TO INCREASE BIOPRODUCT TOLERANCE, TITER, OR OSMOTIC SHOCK TOLERANCE

(75) Inventor: Jeanette M. Mucha, San Carlos, CA (US)

(73) Assignee: Cobalt Technologies, Inc., Mountain View, CA (US)

( * ) Notice: Subject to any disclaimer, the term of this patent is extended or adjusted under 35 U.S.C. 154(b) by 0 days.

(21) Appl. No.: 13/159,293

(22) Filed: Jun. 13, 2011

(65) Prior Publication Data

US 2011/0306083 A1    Dec. 15, 2011

Related U.S. Application Data

(60) Provisional application No. 61/354,567, filed on Jun. 14, 2010.

(51) Int. Cl.
*C12Q 1/02* (2006.01)
*C12P 21/06* (2006.01)
*C12P 1/04* (2006.01)
*C12N 1/20* (2006.01)

(52) U.S. Cl. ....... 435/29; 435/69.1; 435/170; 435/252.7
(58) Field of Classification Search .................. 435/170, 435/29, 252.7, 69.1
See application file for complete search history.

(56) References Cited

U.S. PATENT DOCUMENTS

| | | | |
|---|---|---|---|
| 5,192,673 A | 3/1993 | Jain et al. | |
| 5,859,337 A | 1/1999 | Gasser et al. | |
| 2007/0122869 A1 | 5/2007 | Hasegawa et al. | |
| 2009/0191593 A1 | 7/2009 | Burk et al. | |
| 2010/0120106 A1 | 5/2010 | Kohn et al. | |

OTHER PUBLICATIONS

Ezeji et al. (2007) Butanol production from agricultural residues: Impact of degradation products on *Clostridium beijerinckii* growth and butanol fermentation, Biotechnology and Bioengineering, vol. 97, No. 6, Aug. 15, 2007.*
Anderson et al. (2011) Identification of RCN1 and PSA3 as ethanol-tolerant genes in *Saccharomyces cerevisiae* using a high copy barcoded library, FEMS Yeast Research, 1-13.*
Ezeji et al. (2007) Bioproduction of butanol from biomass: from genes to bioreactors, Current Opinion in Biotechnology, 18: 220-227.*
Fischer et al. (2008) Selection and optimization of microbial hosts for biofuels production, Metabolic Engineering, 10: 295-304.*
Liu et al. (2010) Butanol production by *Clostridium beijerinckii* ATCC 55025, J Ind Microbiol Biotechnol, 37: 495-501.*
Maddox et al. (1995) Production of acetone-butanol-ethanol from concentrated substrates using *Clostridium acetobutylicum* in an integrated fermentation-product removal process, Process Biochemistry, vol. 30, No. 3, pp. 209-215.*
Tomas et al. Transcriptional analysis of butanol stress and tolerance in *Clostridium acetobutylicum*, Journal of Bacteriology, Apr. 2004, p. 2006-2018.*
Walter et al. (1987) The roles of osmotic stress and water activity in the inhibition of the growth, glycolysis and glucose phosphotransferase system of *Clostridium pasteurianum*, Journal of General Microbiology, 133, 259-266.*
Lynd et al. (2001) Salt accumulation resulting from base added for pH control, and not ethanol, limits growth of *Thermoanaerobacterium thermosaccharolyticum* HG-8 at elevated feed xylose concentrations in continuous culture, Biotechnol. Prog., 17: 118-125.*
Bargmann, et al. Multiple PLDs required for high salinity and water deficit tolerance in plants. Plant Cell Physiol. Jan. 2009;50(1):78-89. Epub Nov. 18, 2008.
Dunlap, et al. Osmotic shock tolerance and membrane fluidity of cold-adapted *Cryptococcus flavescens* OH 182.9, previously reported as *C. nodaensis*, a biocontrol agent of *Fusarium* head blight. FEMS Yeast Res. May 2007;7(3):449-58. Epub Jan. 18, 2007.
Rigden. A distant evolutionary relationship between GPI-specific phospholipase D and bacterial phosphatidylcholine-preferring phospholipase C. FEBS Lett. Jul. 2, 2004;569(1-3):229-34.
Spiegelberg. Sugar and Salt Tolerance of *Clostridium pasteurianum* and Some Related Anaerobes. J Bacteriol. Jul. 1944;48(1):13-30.
Tanaka, et al. Microsomal phosphatidic acid phosphohydrolase of rat mammary tissue: I. General properties. Lipids. Jan. 1980;15(1):26-32.
International search report and written opinion dated Dec. 28, 2011 for PCT/US2011/040226.

\* cited by examiner

*Primary Examiner* — Karen Cochrane Carlson
*Assistant Examiner* — Jennifer M. H. Tichy
(74) *Attorney, Agent, or Firm* — Wilson Sonsini Goodrich & Rosati

(57) ABSTRACT

Methods are provided for selecting microbial strains with improved properties for fermentation and/or bioproduct production. A salt selection is employed to identify mutants with improved bioproduct tolerance, titer, or osmotic tolerance relative to a microbial strain from which they were derived.

12 Claims, 8 Drawing Sheets

2A

2B

4A

4B

5A

5B

SALT SELECTION OF MICROBIAL MUTANTS TO INCREASE BIOPRODUCT TOLERANCE, TITER, OR OSMOTIC SHOCK TOLERANCE

CROSS-REFERENCE TO RELATED APPLICATIONS

This application claims the benefit of U.S. Provisional Application No. 61/354,567, filed Jun. 14, 2010, which is incorporated by reference herein in its entirety.

FIELD OF THE INVENTION

The invention relates to a salt selection method to identify mutant microbial strains with improved properties such as bioproduct tolerance, titer, and/or osmotic shock tolerance.

BACKGROUND OF THE INVENTION

Butanol is a high quality fuel and fuel additive. Butanol can be mixed, stored and transported together with gasoline. It has more energy per gallon than ethanol, which translates into better fuel economy for consumers using butanol blends, and has lower vapor pressure than ethanol, which translates into less ground level pollution. Butanol's low vapor pressure makes it an attractive low volatility, oxygenated, blend component for refiners to use in complying with stringent vapor pressure specifications. Butanol can provide the oxygenate benefits of ethanol but without undue evaporative emissions, which are a significant source of air pollution, and at a potentially lower cost. Butanol is also more hydrophobic than ethanol, i.e., it has a higher tendency to repel water, and is more suitable for blending with gasoline. As such, butanol should be a highly desired component of Reformulated Gasoline Blendstock for Oxygenate Blending (RBOB) and California (CARBOB) fuel blendstock. Butanol is also expected to have a reduced life cycle emission of $CO_2$. Butanol blends should have no detrimental effects on modern fuel system elastomers, and corrosion and electrical conductivity are expected to be similar to gasoline.

Butanol is also widely used as an industrial chemical. It is used in the production of paints, plasticizers, and pesticides, as an ingredient in contact lens cleansers, cement, and textiles, and also as a flavoring in candy and ice cream. The global market for n-butanol was approximately 1 billion gallons in 2006; the U.S. market was approximately 300 million gallons, and is expected to grow approximately 2% per year.

Butanol is currently made from petroleum. Production costs are high and margins are low, and price trends generally track the price of oil and are heavily influenced by global economic growth. There is a need for improved methods for production of butanol. In particular, methods for environmentally compatible, cost efficient, and energy efficient production of butanol would be desirable.

Industrial scale fermentations were historically performed for solvent and acid production prior to the rise of the petrochemical industry. Concerns about pollution, climate change, and resulting environmental degradation have renewed interest, particularly where low cost or waste biomatter are available as feedstock. One problem that economically constrains more widespread adoption is the high energy expenditure required to recover fermentation products from the low concentrations typically seen in fermentation broths. Efforts to increase product concentrations in fermentation broths have met with limited success owing to the toxicity of these compounds to the cultured microorganisms. Another issue which constrains the economic feasibility of fermentation based bioproducts is the productivity of the fermentation process. Increases in productivity lead to an improved use of installed capital.

Methods for producing microbial strains with improved butanol tolerance and fermentation titer have involved selection in butanol-containing liquid culture medium or on butanol-containing agar plates. Liquid medium or plates containing high butanol concentrations release butanol vapors through evaporation, which causes unfavorable environmental conditions for workers. Evaporation also makes it difficult to regulate the concentration of butanol in plate or liquid culture. There is a need for an improved method for selecting microbial strains with increased butanol tolerance or titer using a screening method that does not include addition of butanol to the growth medium.

BRIEF SUMMARY OF TILE INVENTION

Methods for Methods for producing and selecting microbial strains with increased tolerance to a bioproduct that is produced by and toxic to the cells, production titer of a bioproduct, and/or increased osmotic tolerance are provided herein. The methods include selection on medium that includes added salt in a concentration sufficient to significantly inhibit growth of a parent strain, e.g., a solvent-producing parent strain, and selection of cells that grow in the presence of the salt. Microbial cells that are selected in accordance with the methods described herein, and methods for producing a bioproduct, such as a solvent, in such cells, are also provided.

In one aspect, a method is provided for selecting a microbial strain with increased tolerance to one or more bioproduct(s) that is(are) produced by and toxic to the cells, e.g., one or more solvent(s). The method includes culturing mutants of a bioproduct-producing microbial parent strain on solid growth medium or in liquid growth medium that contains salt added at a concentration sufficient to significantly inhibit growth of the parent strain, for example, by at least about 99%, selecting microbial colonies that grow in the presence of the added salt, and identifying a microbial strain that is more tolerant to the bioproduct(s) than the parent strain by assessing tolerance of the colonies to the bioproduct(s).

In one embodiment, the method includes culturing mutants of a solvent-producing microbial strain on solid growth medium or in liquid growth medium that contains salt added at a concentration sufficient to significantly inhibit growth of the solvent-producing microbial strain, for example, by at least about 99%, selecting microbial colonies that grow in the presence of the added salt, and identifying a solvent tolerant microbial strain by assessing the tolerance of the colonies to one or more solvent(s). In some embodiments, solvent tolerance is at least about 5% higher to at least one solvent in the solvent tolerant microbial strain than in the solvent-producing microbial strain from which it was derived.

In some embodiments, the strain produces butanol, acetone, and/or ethanol. In one embodiment, the strain produces butanol. In one embodiment, the salt added to the growth medium is at a concentration of at least about 50 mM.

The microbial strain may be bacterial or fungal. In some embodiments, the microbial strain is a bacterial species of *Clostridium*, *Lactobacillus*, *Enterococcus*, *Escherichia*, *Bacillus*, *Pichia*, *Pseudomonas*, *Synechocystis*, or *Saccharomyces*. In one embodiment, the bacterial strain is a *Clostridium* species, for example, *Clostridium acetobutylicum*, *Clostridium beijerinckii*, *Clostridium saccharobutylicum*, *Clostridium puniceum*, *Clostridium saccharoperbuty-*

*lacetonicum, Clostridium pasteuranium, Clostridium butylicum, Clostridium aurantibutyricum, Clostridium tetanomorphum, Clostridium thermocellum,* or *Clostridium thermosaccharolyticum*.

The salt used for the selection method may be an organic or inorganic salt, or a mixture thereof. In some embodiments, the salt is sodium chloride, potassium chloride, potassium phosphate, ammonium sulfate, calcium chloride, or calcium phosphate, or a mixture thereof.

In some embodiments, the bioproduct tolerant (e.g., solvent tolerant) microbial strain has an increased tolerance to one or more inhibitor(s) present in hydrolyzed cellulosic feedstock relative to the microbial strain from which it was derived. In some embodiments, the bioproduct tolerant (e.g., solvent tolerant) microbial strain produces the bioproduct(s) (e.g., solvent(s)) at an increased titer. In some embodiments, the bioproduct tolerant (e.g., solvent tolerant) microbial strain has an increased tolerance to osmotic shock.

In some embodiments, the method for selecting a bioproduct tolerant (e.g., solvent tolerant) microbial strain further includes producing a second set of mutants of the selected tolerant microbial strain, culturing the second mutants on solid growth medium or in liquid growth medium containing salt added in an amount sufficient to significantly inhibit microbial growth, for example, by at least about 99%, selecting microbial colonies that grow in the presence of the added salt, and identifying second mutants with a greater tolerance than the tolerant microbial strain from which they were derived by assessing the tolerance of the colonies to one or more bioproduct(s) (e.g., solvent(s)). In some embodiments, tolerance of the second mutants to one or more bioproduct(s) (e.g., solvent(s)) is at least about 5% higher than the tolerance of the microbial strain from which they were derived. In some embodiments, the concentration of salt that is added to the growth medium is higher, for example, at least about 50 mM higher, than the concentration of salt that was added for selection of the tolerant microbial strain from which the second mutants were derived.

In one embodiment, the method for selecting a microbial strain includes with increased tolerance to a bioproduct that is produced by and toxic to the cells includes: (a) contacting bioproduct-producing microbial cells with a mutagen to produce mutants; (b) plating the mutants on solid medium in first selection plates in the presence of a concentration of salt sufficient to inhibit growth of the bioproduct-producing parent cells by at least about 99%; (c) incubating the first selection plates under conditions suitable for growth of microbial colonies; and (d) selecting colonies that grow on the first selection plates. In one embodiment, the method further includes: (e) restreaking the colonies from the first selection plates on second selection plates that contain solid medium with about the same concentration of salt as used in step (b); (f) incubating the second selection plates under conditions suitable for growth of bacterial colonies; (g) selecting colonies that grow on the second selection plates; and (h) assessing tolerance of the colonies that grow on the second selection plates to one or more bioproduct(s) to identify the bioproduct tolerant microbial strain. In some embodiments, tolerance to one or more bioproduct(s) is at least about 5% higher in the bioproduct tolerant microbial stain relative to the bioproduct-producing microbial strain from which it was derived.

In one embodiment, a solvent tolerant microbial strain is selected in a method that includes: (a) contacting solvent-producing microbial cells with a mutagen to produce mutants; (b) plating the mutants on solid medium in first selection plates in the presence of a concentration of salt sufficient to inhibit growth of the solvent-producing parent cells by at least about 99%; (c) incubating the first selection plates under conditions suitable for growth of microbial colonies; and (d) selecting colonies that grow on the first selection plates. In one embodiment, the method further includes: (e) restreaking the colonies from the first selection plates on second selection plates that contain solid medium with about the same concentration of salt as used in step (b); (f) incubating the second selection plates under conditions suitable for growth of bacterial colonies; (g) selecting colonies that grow on the second selection plates; and (h) assessing tolerance of the colonies that grow on the second selection plates to one or more solvent(s) to identify the solvent tolerant microbial strain. In some embodiments, tolerance to one or more solvent(s) is at least about 5% higher in the solvent tolerant microbial stain relative to the solvent-producing microbial strain from which it was derived.

In some embodiments, a bioproduct (e.g., solvent) tolerant microbial strain produced according to the methods herein also produces one or more bioproduct(s) (e.g., solvent(s)) to which the strain has increased tolerance at a higher titer when grown in fermentation medium under conditions suitable for bioproduct (e.g., solvent) production than the bioproduct-producing (e.g., solvent-producing) microbial strain from which it was derived. In some embodiments, the titer of one or more bioproduct(s) (e.g., solvent(s)) is at least about 5% higher in the bioproduct tolerant (e.g., solvent tolerant) strain than the titer of the bioproduct-producing (e.g., solvent-producing) microbial strain from which it was derived. In some embodiments, the bioproduct tolerant (e.g., solvent tolerant) microbial strain also has an increased osmotic tolerance, for example, at least 10% higher osmotic tolerance than the parent strain from which the tolerant strain was derived.

In another aspect, any of the methods described herein may be used to select a microbial strain that produces one or more bioproduct(s) at an increased titer in comparison with a bioproduct producing parent strain. In one embodiment, the bioproduct is a solvent and the method includes culturing mutants of a solvent-producing microbial strain on solid growth medium or in liquid growth medium that contains salt added at a concentration sufficient to significantly inhibit growth of the solvent producing parent strain, for example, at least about 99%, selecting microbial colonies that grow in the presence of the added salt, and identifying a microbial strain that produces one or more solvent(s) at an increased titer by assessing the solvent titer of the colonies when grown in fermentation medium under conditions suitable for solvent production. In some embodiments, titer of one or more solvent(s) in the selected mutant is at least about 5% higher than the titer of the solvent producing parent strain from which it was derived.

In another aspect, any of the methods described herein may be used to select a microbial strain with increased osmotic tolerance in comparison with a parent strain. In one embodiment, the method includes culturing mutants of a parent strain on solid growth medium or in liquid growth medium that contains salt added in an amount sufficient to inhibit growth of the parent strain by at least about 99%, selecting microbial colonies that grow in the presence of the salt, and identifying a microbial strain with increased osmotic tolerance by assessing osmotic tolerance in the selected colonies. In some embodiments, osmotic tolerance in the selected mutant is at least about 10% higher than the osmotic tolerance of the parent strain from which it was derived, i.e., at least about 10% increase in viability in an osmotic shock test. In some embodiments, the parent strain is a bioproduct producing strain, such as a solvent producing strain.

In another aspect, a microbial strain is provided with increased bioproduct tolerance (e.g., solvent tolerance) and/or bioproduct production titer (e.g., solvent production titer) and/or osmotic tolerance, produced according to any of the methods described herein.

In some embodiments, a microbial strain selected according to any of the methods herein contains an altered morphology in comparison to the parent microbial strain from which it was derived. In some embodiments, the altered morphology includes a cell membrane that visually or microscopically appears less rigid and/or more fluid than the membrane of the parent strain, e.g., solvent-producing strain, from which it was derived. In other embodiments, the altered morphology includes a cell membrane that visually or microscopically appears more rigid and/or less fluid than the membrane of the parent strain, e.g., solvent-producing strain from which it was derived.

In some embodiments, the microbial strain exhibits an increased survival when exposed to a mutagenic compound, in comparison to the parent strain, e.g., solvent-producing strain, from which it was derived.

In one embodiment, the mutagenic compound is ethyl methane sulfonate (EMS). In another embodiment, the mutagenic compound is N-methyl-N'-nitro-N-nitrosoguanidine (MNNG). In one embodiment, the mutagenic compound is EMS and the survival is at least about 10% higher. In one embodiment, the mutagenic compound is MNNG and the survival is at least about 80% higher.

In some embodiments, the microbial strain exhibits increased tolerance to one or more inhibitor(s) present in hydrolyzed cellulosic feedstock relative to the parent strain, e.g., solvent-producing strain, from which it was derived.

In some embodiments of the selection methods described herein, salt is added to a medium (e.g., a growth medium or a hydrolysate of biomass, for example, cellulosic biomass, e.g., lignocellulosic biomass) that already contains salt(s) (e.g., NaCl and/or other salt(s)) and/or inhibitor(s) of microbial growth and/or bioproduct (e.g., solvent) production (for example, but not limited to, aliphatic or aromatic acids, aromatic aldehydes, phenols, solvents, or lignins), and this medium to which salt has been added is used in a selection method as described above.

In another aspect, a method is provided for producing one or more bioproduct(s), for example, one or more solvent(s). The method includes culturing a microbial strain, e.g., a solvent-producing microbial strain, with increased solvent tolerance and/or increased solvent production titer and/or increased osmotic tolerance, produced according to any of the methods described herein, under conditions suitable for bioproduct, e.g., solvent production. In some embodiments, the microbial strain is immobilized on a solid support in a bioreactor, e.g., as a biofilm. In some embodiments, the method includes continuously fermenting the microbial strain in the presence of hydrolyzed feedstock. The feedstock is may be hydrolyzed continuously to produce carbohydrate molecules that serve as a carbon source for fermentation and the hydrolyzed feedstock may be fed to the bioreactor continuously for the duration of the fermentation, with the microbial strain continuously converting the hydrolyzed feedstock into bioproduct (e.g., solvent). In some embodiments, the feedstock is a cellulosic material, for example, a lignocellulosic material, e.g., softwood, hardwood, or a combination thereof. In some embodiments, the feedstock hydrolysis includes treatment with an acid, for example, nitric acid, formic acid, acetic acid, or sulfuric acid. In one embodiment, the feedstock is hydrolyzed with nitric acid.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows growth of the parent strain Co-9064 and mutants selected in the salt selection method described in Example 1, in the presence of increasing concentrations of butanol. 4 ml cultures were started at a 1:20 dilution from a log phase seed train. Butanol was added to the cultures in amounts varying from 0 to 1.9 g/l. Optical density at 600 nm was determined at 72 hours. FIG. 2B also shows growth of the parent strain Co-9064 and a mutant selected in the salt selection method described in Example 1, in the presence of increasing concentrations of butanol. Duplicate 4 ml cultures were started at a 1:20 dilution from a log phase seed train. Butanol was added to the cultures in amounts varying from 0 to 2.1 g/l. Optical density at 600 nm was determined at 96 hours.

FIG. 4A shows butanol titers of the mutants selected as described in Example 2 in comparison with the butanol titer of the parent strain. FIG. 4B shows butanol titer distributions for the parent strain (peak at about 15) and mutants (peak at about 5) selected as described in Example 2.

FIG. 5A shows butanol titers of the mutants selected as described in Example 3 in comparison with the butanol titer of the parent strain. FIG. 5B shows butanol titer distributions for the parent strain (peak at about 15) and mutants (peak at about 2) selected as described in Example 3.

FIG. 6 shows the difference in morphology between a parent's and NaCl mutant's Clostridial forms.

DETAILED DESCRIPTION OF THE INVENTION

Figure 1:
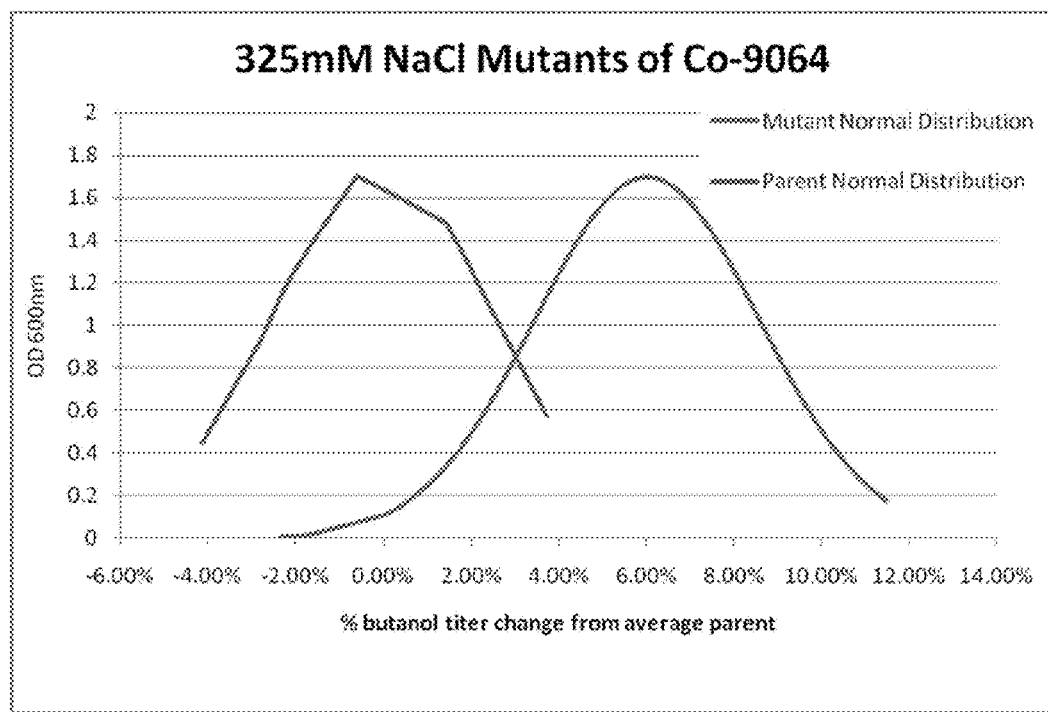
FIG. 1 shows butanol titer distributions for the parent strain Co-9064 (curve on left) and mutants (curve on right) selected in the salt selection method described in Example 1. The data includes 600 mutants and 16 parent controls, grown in liquid medium without salt.

The invention provides methods for selecting microbial strains with improved properties, such as increased bioproduct tolerance and/or bioproduct production titer, for example, increased solvent tolerance and/or solvent production titer, for a bioproduct (e.g., solvent) that is produced by the microbial strain, and/or increased osmotic tolerance. Methods for using the selected strains in fermentative bioproduct, e.g., solvent production process are also described.

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, N.Y. (1991) provide one of skill with a general dictionary of many of the terms used in this invention. Any methods and materials similar or equivalent to those described herein can be used in the practice or testing of the present invention.

Numeric ranges provided herein are inclusive of the numbers defining the range. Unless otherwise indicated, nucleic acids are written left to right in 5' to 3' orientation; amino acid sequences are written left to right in amino to carboxy orientation, respectively.

Definitions

"Biofuel" refers to fuel molecules (e.g., butanol, acetone, and/or ethanol) produced biologically by a microorganism, e.g., in a microbial fermentation process.

"Biobutanol" refers to butanol (i.e., n-butanol) produced biologically by a microorganism, e.g., in a microbial fermentation process.

"Feedstock" refers to a substance that can serve as a source of sugar molecules to support microbial growth in a fermentation process. In some embodiments, the feedstock must be pretreated to release the sugar molecules. In one embodiment, the feedstock is hydrolyzed to release 5 and/or 6 carbon sugar molecules.

"Deconstruction" refers to mechanical, chemical, and/or biological degradation of biomass into to render individual components (e.g., cellulose, hemicellulose) more accessible to further pretreatment processes, for example, a process to release monomeric and oligomeric sugar molecules, such as acid hydrolysis.

"Conditioning" refers to removal of inhibitors of microbial growth and/or bioproduct (e.g., solvent) production from a feedstock or pretreated feedstock (e.g., a hydrolysate produced by hydrolysis of a feedstock).

"Titer" refers to amount of a substance produced by a microorganism per unit volume in a microbial fermentation process. For example, biobutanol titer may be expressed as grams of butanol produced per liter of solution.

"Yield" refers to amount of a product produced from a feed material (for example, sugar) relative to the total amount that of the substance that would be produced if all of the feed substance were converted to product. For example, biobutanol yield may be expressed as % of biobutanol produced relative to a theoretical yield if 100% of the feed substance (for example, sugar) were converted to biobutanol.

"Productivity" refers to the amount of a substance produced by a microorganism per unit volume per unit time in a microbial fermentation process. For example, biobutanol productivity may be expressed as grams of butanol produced per liter of solution per hour.

"Tolerance" of a microorganism to a substance, for example, tolerance to butanol or "butanol tolerance," refers to the ability of a microorganism to grow in the presence of a defined concentration of the substance, e.g., butanol, which typically serves as a barrier to growth of similar microorganisms, for example, a parent or wild-type strain of the microorganism.

"Wild-type" refers to a microorganism as it occurs in nature.

"Parent strain" refers to a microbial strain from which a mutant is derived.

"Biomass" refers to cellulose- and/or starch-containing raw materials, including but not limited to wood chips, corn stover, rice, grasses, forages, perrie-grass, potatoes, tubers, roots, whole ground corn, grape pomace, cobs, grains, wheat, barley, rye, milo, brans, cereals, sugar-containing raw materials (e.g., molasses, fruit materials, sugar cane, or sugar beets), wood, and plant residues.

"Starch" refers to any starch-containing materials. In particular, the term refers to various plant-based materials, including but not limited to wheat, barley, potato, sweet potato, tapioca, corn, maize, cassava, milo, rye, and brans. In general, the term refers to any material comprised of the complex polysaccharide carbohydrates of plants, comprised of amylose, and amylopectin, with the formula $(C_6H_{10}O_5)_x$, wherein "x" can be any number.

"ABE fermentation" refers to production of acetone, butanol, and/or ethanol by a fermenting microorganism.

The term "microbial strain" or "microorganism" refers to bacterial and fungal microorganisms.

The term "culturing" refers to growing a population of cells, e.g., microbial cells, under suitable conditions for growth, in a liquid or solid medium.

The term "derived from" generally indicates that one specified material finds its origin in another specified material or has features that can be described with reference to the another specified material.

"Solvent" refers to a liquid or gas produced by a microorganism that is capable of dissolving a solid or another liquid or gas. Nonlimiting examples of solvents produced by microorganisms include butanol, acetone, and ethanol.

A "protic" solvent contains dissociable $H^+$, for example a hydrogen atom bound to an oxygen atom as in a hydroxyl group or a nitrogen atom as in an amino group. A protic solvent is capable of donating a proton $(H^+)$. Conversely, an "aprotic" solvent cannot donate $H^+$.

The terms "osmotic tolerance" and "osmotic shock tolerance," used interchangeably herein, refer to the ability of a microbial cell to withstand osmotic pressure conditions, such as, for example, high substrate, product, and/or salt concentrations which would typically dehydrate the cell.

"Bioproduct" refers to any substance of interest produced biologically, i.e., via a metabolic pathway, by a microorganism, e.g., in a microbial fermentation process. Bioproducts include, but are not limited to biofuels (e.g., butanol, acetone, ethanol), solvents, biomolecules (e.g., proteins (e.g., enzymes), polysaccharides), organic acids (e.g., formate, acetate, butyrate, propionate, succinate), alcohols (e.g., methanol, propanol, isopropanol, hexanol, 2-butanol, isobutanol), fatty acids, aldehydes, lipids, long chain organic molecules (for example, for use in surfactant production), vitamins, and sugar alcohols (e.g., xylitol).

The abbreviation "MIC" refers to minimum inhibitory concentration.

"A," "an" and "the" include plural references unless the context clearly dictates otherwise.

"ATCC" refers to the American Type Culture Collection, P.O. Box 1549, Manassas, Va. 20108.

Methods for Selecting Tolerant Microbial Strains

Methods are provided for selecting a microbial strain with increased tolerance to a bioproduct that is produced by and toxic to the cells. In one embodiment, the bioproduct is a solvent. A bioproduct-producing parent strain, such as a solvent-producing strain, is mutagenized to produce mutants. The mutants are cultured on solid or liquid growth medium to which salt has been added ("salt selection medium"). In some embodiments, salt is added at a concentration sufficient to inhibit growth of the parent strain by at least about 90, 95, 98, or 99%. In some embodiments, the salt selection medium contains any of about 50 mM to about 500 mM, about 50 mM to about 150 mM, about 100 mM to about 250 mM, about 200 mM to about 400 mM, about 300 mM to about 450 mM, about 400 mM to about 550 mM, or about 100 mM to about 900 mM salt. In some embodiments, the salt selection medium contains any of about 50, 100, 150, 200, 250, 300, 350, 400, 450, 500, 550, 600, 650, 700, 750, 800, 850, or 900 mM salt. In some embodiments, the salt selection medium contains any of about 50, 100, 150, 200, 250, 300, or 350 mM to any of about 400, 450, 500, 550, 600, 650, 700, 750, 800, 850, or 900 mM salt.

Microbial colonies that grow in the presence of the added salt are selected. Tolerant mutants are selected by assessing tolerance of the colonies selected by growth in the presence of salt to the bioproduct. In some embodiments, the parent strain is a solvent-producing strain and solvent tolerant mutants are selected by assessing solvent tolerance of the colonies selected by growth in the presence of salt. Solvent tolerance may be assessed by determining the concentration of solvent in which the selected mutant can grow to 50% of the optical density reached in media without solvent and compared to the concentration of solvent in which the parent can grow to 50% of the optical density reached in media without solvent.

The following procedure may be used to assess solvent tolerance of a mutant microbial strain in comparison to a parent strain: (1) Determine the $OD_{600}$ (optical density at 600 nm) for cultures of both the mutant and parent strains at with no added solvent at an appropriate time point, for example, a time point at which the majority of the cells have completed solventogenesis. (In some embodiments in which a Clostridia strain is used, the time point may be, for example, 72 hours). (2) Determine the $OD_{600}$ for cultures of both the mutant and parent strains at an appropriate time point, for example, a time point at which the majority of the cells have completed solventogenesis. (In some embodiments in which a Clostridia strain is used, the time point may be, for example, 72 hours) with varying amounts of solvent added at inoculation (for example, 0.5-2.5% butanol (v/v)). (3) Graph the $OD_{600}$ for both the parent and mutant for each solvent concentration tested. (4) Draw a line between the two points on the graph between which 50% inhibition is observed with respect to the $OD_{600}$ observed in (1). Do this for both the parent and the mutant. (5) Using the equation for each line, determine the percentage of added solvent that would result in 50% inhibition. (6) Determine the percentage of solvent tolerance improvement by first subtracting the parent's OD at 50% inhibition from the mutant's OD at 50% inhibition. Take this difference and divide it by the parent's OD at 50% inhibition. Multiply this number by 100.

An example of assessment of solvent tolerance improvement for two mutants is provided in Table 1 below.

TABLE 1

| | OD with no added solvent | 50% inhibition OD | % of added n-butanol (v/v) at 50% inhibition | % improvement |
|---|---|---|---|---|
| parent | 6.12 | 3.06 | 0.98 | |
| mutant #1 | 5.25 | 2.62 | 1.18 | 20.89% |
| mutant #2 | 3.62 | 1.81 | 1.66 | 69.96% |

In some embodiments, the tolerance of a bioproduct tolerant mutant, such as a solvent tolerant mutant, is at least about 5%, 10%, 20%, 25%, 30%, 40%, 50%, 60%, 70%, 80%, 90%, or 100% higher than the bioproduct tolerance (e.g., solvent tolerance) in the parent strain from which the mutant was derived. In one embodiment, bioproduct tolerance (e.g., solvent tolerance) of the bioproduct tolerant (e.g., solvent tolerant) mutant is about 5% to about 100%, or about 8% to about 36%, higher than the bioproduct (e.g., solvent) tolerance in the parent strain from which the mutant was derived. In some embodiments, the bioproduct (e.g., solvent) tolerance is any of about 5%, 10%, 20%, 25%, 30%, or 40% to any of about 50%, 60%, 70%, 80%, 90%, or 100% higher in the bioproduct tolerant (e.g., solvent tolerant) mutant than the parent strain from which it was derived.

In one embodiment, a method for selecting a bioproduct tolerant microbial strain includes: (a) contacting bioproduct-producing microbial cells with a mutagen to produce mutants; (b) plating the mutants on solid medium in selection plates that contain salt selection medium with a concentration of salt sufficient to inhibit growth of the bioproduct-producing parent strain by at least about 90, 95, 98, or 99%; (c) incubating the selection plates under conditions suitable for growth of microbial colonies; (d) selecting colonies that grow on the selection plates; and (e) assessing bioproduct tolerance of colonies that grow on the selection plates to identify a bioproduct tolerant microbial strain. In one embodiment, bioproduct tolerance is at least about 5% higher in the bioproduct tolerant microbial strain relative to the bioproduct-producing parent strain from which it was derived. Optionally, prior to step (e), colonies that grow on the first selection plates (step (d)) may be restreaked on second selection plates that comprise salt in a concentration that is substantially the same as the first selection plates, followed by incubation of the second selection plates under conditions suitable for growth of bacterial colonies, and selection of colonies that grow on the second selection plates. Colonies that grow on the second selection plates are then assessed for bioproduct tolerance to identify strains with greater bioproduct tolerance, for example, at least about 5% greater bioproduct tolerance, than the bioproduct-producing parent microbial strain from which the mutants were derived.

In one embodiment, a method for selecting a solvent tolerant microbial strain includes: (a) contacting solvent-producing microbial cells with a mutagen to produce mutants; (b) plating the mutants on solid medium in selection plates that contain salt selection medium with a concentration of salt sufficient to inhibit growth of the solvent-producing parent strain by at least about 90, 95, 98, or 99%; (c) incubating the selection plates under conditions suitable for growth of microbial colonies; (d) selecting colonies that grow on the selection plates; and (e) assessing solvent tolerance of colonies that grow on the selection plates to identify a solvent tolerant microbial strain. In one embodiment, solvent tolerance is at least about 5% higher in the solvent tolerant microbial strain relative to the solvent-producing parent strain from which it was derived. Optionally, prior to step (e), colonies that grow on the first selection plates (step (d)) may be restreaked on second selection plates that comprise salt in a concentration that is substantially the same as the first selection plates, followed by incubation of the second selection plates under conditions suitable for growth of bacterial colonies, and selection of colonies that grow on the second selection plates. Colonies that grow on the second selection plates are then assessed for solvent tolerance to identify strains with greater solvent tolerance, for example, at least about 5% greater solvent tolerance, than the solvent-producing parent microbial strain from which the mutants were derived.

The salt used for selection may be organic or inorganic, or a combination thereof. In some embodiments, the salt used for the selection is an inorganic salt. Nonlimiting examples of inorganic salts that may be used for the selection method include sodium chloride, potassium chloride, potassium phosphate, ammonium sulfate, calcium chloride, and calcium phosphate, or a mixture thereof. In one embodiment, the salt is sodium chloride. In one embodiment, salt(s) are present in the salt selection medium at a total concentration of about 50 mM to about 500 mM, about 50 mM to about 150 mM, about 100 mM to about 250 mM, about 200 mM to about 400 mM, about 300 mM to about 450 mM, about 400 to about 550 mM, or about 100 mM to about 900 mM. In some embodiments, salt(s) are present in the salt selection medium at a total concentration of any of about 50, 100, 150, 200, 250, 300, 350, 400, 450, 500, 550, 600, 650, 700, 750, 800, 850, or 900 mM. In some embodiments, salt(s) are present in the salt selection medium at a total concentration of any of about 50, 100, 150, 200, 250, 300, or 350 mM to any of about 400, 450, 500, 550, 600, 650, 700, 750, 800, 850, or 900 mM.

In some embodiments, the salt selection medium is produced by adding salt to a medium that already contains salt(s) and/or inhibitor(s) of microbial growth and/or bioproduct (e.g., solvent) production.

The microbial parent strain may be bacterial or fungal. In one embodiment, the microbial strain is bacterial, for example, selected from the genera *Clostridium, Lactobacillus, Enterococcus, Escherichia, Bacillus, Pichia, Pseudomonas, Synechocystis*, or *Saccharomyces*. In some embodiments, the microbial strain is a *Clostridium* species, for example, *Clostridium acetobutylicum, Clostridium beijerinckii, Clostridium saccharobutylicum, Clostridium puniceum, Clostridium saccharoperbutylacetonicum, Clostridium pasteuranium, Clostridium butylicum, Clostridium aurantibutyricum, Clostridium tetanomorphum, Clostridium thermocellum*, and *Clostridium thermosaccharolyticum*.

In some embodiments, the bioproduct is a solvent and the solvent that is produced by the parent strain and that the mutants are selected for increased tolerance to is a polar aprotic or protic solvent. In some embodiments, the solvent is selected from n-butanol, acetic acid, isopropanol, n-propanol, ethanol, methanol, formic acid, 1,4-dioxane, tetrahydrofuran, acetone, acetonitrile, dimethylformamide, or dimethyl sulfoxide, or a combination thereof. In one embodiment, the solvent is n-butanol (also referred to as "butanol" herein).

In some embodiments, a mutant with increased bioproduct (e.g., solvent) tolerance produced as described herein also produces the bioproduct at a higher titer than the parent strain from which the mutant was derived, when grown in fermentation medium under conditions suitable for bioproduct (e.g., solvent) production. In some embodiments, the titer is at least about 5%, 10%, 25%, 50%, 75%, 100%, 125%, 150%, 175%, or 200% higher in the bioproduct (e.g., solvent) tolerant mutant than the parent strain. In one embodiment, the titer is about 5% to about 200% higher in the mutant than the parent strain. In some embodiments, the titer is any of about 5%, 10%, 25%, 50%, or 75% to any of about 100%, 125%, 150%, 175%, or 200% higher in the mutant than the parent strain.

In some embodiments, a mutant with increased bioproduct (e.g., solvent) tolerance produced as described herein also exhibits an increased tolerance to inhibitor(s) of microbial growth and/or bioproduct (e.g., solvent) production that are present in hydrolyzed feedstock, relative to the bioproduct producing (e.g., solvent producing) microbial strain from which it was derived. In some embodiments, the mutant exhibits at least about 10, 20, 30, 40, or 50% improvement in growth and/or bioproduct (e.g., solvent) production in the presence of untreated hydrolyzed feedstock (for example, acid hydrolyzed lignocellulosic feedstock) in comparison with the parent strain from which it was derived. Examples of inhibitors that may be present in hydrolyzed feedstock include, but are not limited to, 5-hydroxyy-methyl furfural (HMF), furfural, aliphatic acids, levulinic acid, acetic acid, formic acid, phenolic compounds, vanillin, dihydroconiferylalcohol, coniferyl aldehyde, vanillic acid, hydroquinone, catechol, acetoguaiacone, vanillic acid, homovanillic acid, vanillin, Hibbert's ketones, ammonium nitrate, p-coumaric acid, ferulic acid, 4-hydroxybenzoic acid, syringaldehyde, galacturonic acid, and glucuronic acid.

In some embodiments, a mutant with increased bioproduct (e.g., solvent) tolerance produced as described herein also exhibits both an increased bioproduct (e.g., solvent) titer and an increased tolerance to inhibitor(s) present in hydrolyzed feedstock, as described above. In some embodiments, a mutant with increased bioproduct (e.g., solvent) tolerance produced as described herein exhibits an increased osmotic tolerance.

In some embodiments, second or further rounds of selection are performed. For example, a mutant selected for increased bioproduct (e.g., solvent) tolerance as described above ("first mutant strain") may be further mutagenized to produce "second mutants." The second mutants are cultured on salt selection medium that may contain the same or different (higher or lower) concentration of salt as was added in the first round of selection from which the first mutant strain was selected. Salt may be included in the salt selection medium in a concentration sufficient to inhibit growth of the first mutant strain by at least about 90, 95, 98, or 99%. In one embodiment, the salt selection medium for the second round of selection contains more salt than the salt selection medium that was used for selection of the first mutant strain. In some embodiments, about 50 mM or 100 mM more salt is included in the salt selection medium for the second round of selection than was included for the first round of selection. In some embodiments, the salt selection medium contains about 200 mM to about 900 mM salt. Bioproduct (e.g., solvent) tolerance is assessed for colonies that grow in the presence of salt, and second mutants are identified that have a higher solvent tolerance than the first mutant strain. In some embodiments, bioproduct (e.g., solvent) tolerance of a second mutant strain is at least about 5% higher than the bioproduct (e.g., solvent) tolerance in the first mutant strain from which the second mutant was derived. In some embodiments, second mutant strains exhibit an increased bioproduct (e.g., solvent) titer and/or an increased tolerance to inhibitor(s) of microbial growth and/or bioproduct (e.g., solvent) production that are present in hydrolyzed feedstock, and/or increased osmotic tolerance, relative to the first mutant strain, in addition to increased bioproduct (e.g., solvent) tolerance. One or more further rounds of selection (third, fourth, fifth, etc.) may be performed if desired to obtain strains with further improved bioproduct (e.g., solvent) tolerance, bioproduct (e.g., solvent) titer, tolerance to inhibitor(s) in hydrolyzed feedstock, and/or osmotic tolerance.

Methods for Selecting Microbial Strains with Increased Bioproduct Production Titer Methods are provided for selecting a microbial strain that produces a bioproduct, at an increased titer in comparison with a bioproduct-producing parent strain. In one embodiment, the bioproduct is a solvent. A bioproduct-producing parent strain, such as a solvent-producing parent strain, is mutagenized to produce mutants, and mutants that grow on salt selection medium are assessed for increased bioproduct (e.g., solvent) titer. In some embodiments, salt is added at a concentration sufficient to inhibit growth of the parent strain by at least about 90, 95, 98, or 99%. In some embodiments, the salt selection medium contains about 50 mM to about 500 mM, about 50 mM to about 150 mM, about 100 mM to about 250 mM, about 200 mM to about 400 mM, about 300 mM to about 450 mM, about 400 mM to about 550 mM, or about 100 mM to about 900 mM salt. In some embodiments, the salt selection medium contains any of about 50, 100, 150, 200, 250, 300, 350, 400, 450, 500, 550, 600, 650, 700, 750, 800, 850, or 900 mM salt. In some embodiments, the salt selection medium contains any of about 50, 100, 150, 200, 250, 300, or 350 mM to any of about 400, 450, 500, 550, 600, 650, 700, 750, 800, 850, or 900 mM salt.

Mutants that produce bioproduct, such as a solvent, at a higher titer than the parent strain, such as a solvent-producing parent strain, from which the mutants were derived are selected by assessing bioproduct (e.g., solvent) titer of the colonies that grow in the salt selection medium. Titer is assessed by growing the salt tolerant colonies in fermentation medium under conditions suitable for bioproduct (e.g., solvent) production, and quantitating the bioproduct (e.g., solvent) produced. In some embodiments, the titer is at least about 5%, 10%, 25%, 50%, 75%, 100%, 125%, 150%, 175%, or 200% higher in the selected mutant than in the parent strain. In one embodiment, the titer is about 5% to about 200% higher in the selected mutant than the parent strain. In some embodiments, the titer is any of about 5%, 10%, 25%, 50%, or 75% to any of about 100%, 125%, 150%, 175%, or 200% higher in the selected mutant than the parent strain.

In one embodiment, a method for selecting a microbial strain with increased bioproduct titer includes: (a) contacting bioproduct-producing microbial cells with a mutagen to produce mutants; (b) plating the mutants on solid medium in selection plates that contain salt selection medium with a concentration of salt sufficient to inhibit growth of the bioproduct producing parent strain by at least about 90, 95, 98, or 99%; (c) incubating the selection plates under conditions suitable for growth of microbial colonies; (d) selecting colonies that grow on the first selection plates; and (e) assessing bioproduct titer for colonies that grow on the selection plates to identify a microbial strain with increased bioproduct titer. In one embodiment, bioproduct titer is at least about 5% higher than the bioproduct-producing parent strain from which it was derived. Optionally, prior to step (e), colonies that grow on the first selection plates (step (d)) may be restreaked on second selection plates that contain salt in a concentration that is substantially the same as the first selection plates, followed by incubation of the second selection plates under conditions suitable for growth of bacterial colonies, and selection of colonies that grow on the second selection plates. Colonies that grow on the second selection plates are then assessed for bioproduct titer to identify strains with greater bioproduct titer, for example, at least about 5% greater bioproduct titer, than the bioproduct-producing parent microbial strain from which the mutants were derived.

In one embodiment, a method for selecting a microbial strain with increased solvent titer includes: (a) contacting solvent-producing microbial cells with a mutagen to produce mutants; (b) plating the mutants on solid medium in selection plates that contain salt selection medium with a concentration of salt sufficient to inhibit growth of the solvent producing parent strain by at least about 90, 95, 98, or 99%; (c) incubating the selection plates under conditions suitable for growth of microbial colonies; (d) selecting colonies that grow on the first selection plates; and (e) assessing solvent titer for colonies that grow on the selection plates to identify a microbial strain with increased solvent titer. In one embodiment, solvent titer is at least about 5% higher than the solvent-producing parent strain from which it was derived. Optionally, prior to step (e), colonies that grow on the first selection plates (step (d)) may be restreaked on second selection plates that contain salt in a concentration that is substantially the same as the first selection plates, followed by incubation of the second selection plates under conditions suitable for growth of bacterial colonies, and selection of colonies that grow on the second selection plates. Colonies that grow on the second selection plates are then assessed for solvent titer to identify strains with greater solvent titer, for example, at least about 5% greater solvent titer, than the solvent-producing parent microbial strain from which the mutants were derived.

The salt used for selection may be organic or inorganic, or a combination thereof. In some embodiments, the salt used for the selection is an inorganic salt. Nonlimiting examples of inorganic salts that may be used for the selection method include sodium chloride, potassium chloride, potassium phosphate, ammonium sulfate, calcium chloride, and calcium phosphate, or a mixture thereof. In one embodiment, the salt is sodium chloride. In one embodiment, salt(s) are present in the salt selection medium at a total concentration of about 50 mM to about 500 mM, about 50 mM to about 150 mM, about 100 mM to about 250 mM, about 200 mM to about 400 mM, about 300 mM to about 450 mM, about 400 mM to about 550 mM, or about 100 mM to about 900 mM. In some embodiments, salt(s) are present in the salt selection medium at a total concentration of any of about 50, 100, 150, 200, 250, 300, 350, 400, 450, 500, 550, 600, 650, 700, 750, 800, 850, or 900 mM. In some embodiments, salt(s) are present in the salt selection medium at a total concentration of any of about 50, 100, 150, 200, 250, 300, or 350 mM to any of about 400, 450, 500, 550, 600, 650, 700, 750, 800, 850, or 900 mM.

In some embodiments, the salt selection medium is produced by adding salt to a medium that already contains salt(s) and/or inhibitor(s) of microbial growth and/or bioproduct (e.g., solvent) production.

The microbial parent strain may be bacterial or fungal. In one embodiment, the microbial strain is bacterial, for example, selected from the genera *Clostridium, Lactobacillus, Enterococcus, Escherichia, Bacillus, Pichia, Pseudomonas, Synechocystis,* or *Saccharomyces*. In some embodiments, the microbial strain is a *Clostridium* species, for example, *Clostridium acetobutylicum, Clostridium beijerinckii, Clostridium saccharobutylicum, Clostridium puniceum, Clostridium saccharoperbutylacetonicum, Clostridium pasteuranium, Clostridium butylicum, Clostridium aurantibutyricum, Clostridium tetanomorphum, Clostridium thermocellum,* and *Clostridium thermosaccharolyticum*.

In some embodiments, the bioproduct is a solvent and the solvent that is produced by the parent strain and that the mutants are selected for increased titer of is a polar aprotic or protic solvent. In some embodiments, the solvent is selected from n-butanol, acetic acid, isopropanol, ethanol, methanol, formic acid, 1,4-dioxane, tetrahydrofuran, acetone, acetonitrile, dimethylformamide, or dimethyl sulfoxide, or a combination thereof. In one embodiment, the solvent is n-butanol.

In some embodiments, a mutant that produces a bioproduct (e.g., solvent) at an increased titer produced as described herein also has tolerance to the bioproduct (e.g., solvent) that is produced at increased titer, in comparison with the parent strain from which the mutant was derived, when grown in fermentation medium under conditions suitable for bioproduct (e.g., solvent) production. In some embodiments, the bioproduct (e.g., solvent) tolerance is at least about 5%, 10%, 20%, 25%, 30%, 40%, 50%, 60%, 70%, 80%, 90%, or 100% higher than the tolerance in the parent strain from which the mutant was derived. In one embodiment, bioproduct (e.g., solvent) tolerance of the mutant is about 5% to about 100%, or about 8% to about 36%, higher than the tolerance in the parent strain from which the mutant was derived. In some embodiments, the bioproduct (e.g., solvent) tolerance is any of about 5%, 10%, 20%, 25%, 30%, or 40% to any of about 50%, 60%, 70%, 80%, 90%, or 100% higher in the bioproduct (e.g., solvent) tolerant mutant than the parent strain from which it was derived.

In some embodiments, a mutant with increased bioproduct (e.g., solvent) titer, produced as described herein, also exhibits an increased tolerance to inhibitor(s) of microbial growth and/or bioproduct (e.g., solvent) production that are present in hydrolyzed feedstock, relative to the bioproduct (e.g., solvent) producing microbial strain from which it was derived. In some embodiments, the mutant exhibits at least about 10, 20, 30, 40, or 50% improvement in growth and/or bioproduct (e.g., solvent) production in the presence of untreated hydrolyzed feedstock (for example, acid hydrolyzed lignocellulosic feedstock) in comparison with the parent strain from which it was derived. Example of inhibitors that may be present in hydrolyzed feedstock include, but are not limited to, 5-hydroxyy-methyl furfural (HMF), furfural, aliphatic acids, levulinic acid, acetic acid, formic acid, phenolic compounds, vanillin, dihydroconiferylalcohol, coniferyl aldehyde, vanillic acid, hydroquinone, catechol, acetoguaiacone, vanillic acid, homovanillic acid, vanillin, Hibbert's ketones, ammonium nitrate, p-coumaric acid, ferulic acid, 4-hydroxybenzoic acid, syringaldehyde, galacturonic acid, and glucuronic acid.

In some embodiments, a mutant with increased bioproduct (e.g., solvent) titer produced as described herein also exhibits both an increased bioproduct (e.g., solvent) tolerance and an increased tolerance to inhibitor(s) present in hydrolyzed feedstock, as described above. In some embodiments, a mutant with increased bioproduct (e.g., solvent) titer produced as described herein exhibits an increased osmotic tolerance.

In some embodiments, second or further rounds of selection are performed. For example, a mutant selected for increased bioproduct (e.g., solvent) titer as described above ("first mutant strain") may be further mutagenized to produce "second mutants." The second mutants are cultured on salt selection medium that may contain the same or different (higher or lower) amount of salt that was added in the first round of selection from which the first mutant strain was selected. Salt may be included in the salt selection medium in an amount sufficient to inhibit growth of the first mutant strain by at least about 90, 95, 98, or 99%. In one embodiment, the salt selection medium for the second round of selection contains more salt than the salt selection medium that was used for selection of the first mutant strain. In some embodiments, about 50 mM more salt is included in the salt selection medium for the second round of selection than was included for the first round of selection. In some embodiments, about 100 mM more salt is included in the salt selection medium for the second round of selection than was included for the first round of selection. In some embodiments, the salt selection medium contains about 400 mM to about 550 mM. Bioproduct (e.g., solvent) titer is assessed for colonies that grow in the presence of salt, and second mutants are identified that have a higher bioproduct (e.g., solvent) titer than the first mutant strain. In some embodiments, bioproduct (e.g., solvent) titer of a second mutant strain is at least about 10% higher than the bioproduct (e.g., solvent) tolerance in the first mutant strain from which the second mutant was derived. In some embodiments, second mutant strains exhibit an increased bioproduct (e.g., solvent) tolerance and/or an increased tolerance to inhibitor(s) of microbial growth and/or bioproduct (e.g., solvent) production that are present in hydrolyzed feedstock, and/or increased osmotic tolerance, relative to the first mutant strain, in addition to increased bioproduct (e.g., solvent) titer. One or more further rounds of selection (third, fourth, fifth, etc.) may be performed if desired to obtain strains with further improved bioproduct (e.g., solvent) tolerance, bioproduct (e.g., solvent) titer, and/or tolerance to inhibitor(s) in hydrolyzed feedstock, and/or osmotic tolerance.

Methods for Selecting Microbial Strains with Increased Osmotic Tolerance

Methods are provided for selecting a microbial strain with increased osmotic tolerance in comparison with a parent strain. A parent strain is mutagenized to produce mutants, and mutants that grow on salt selection medium are assessed for increased osmotic tolerance. Mutants that have a higher osmotic tolerance than the parent strain from which the mutants were derived are selected by assessing osmotic tolerance of the colonies that grow in the salt selection medium. In one embodiment, the parent strain is a solvent-producing microbial strain.

In some embodiments, salt is added at a concentration sufficient to inhibit growth of the parent strain by at least about 90, 95, 98, or 99%. In some embodiments, the salt selection medium contains about 50 mM to about 500 mM, about 50 mM to about 150 mM, about 100 mM to about 250 mM, about 200 mM to about 400 mM, about 300 mM to about 450 mM, about 400 mM to about 550 mM, or about 100 mM to about 900 mM salt. In some embodiments, the salt selection medium contains any of about 50, 100, 150, 200, 250, 300, 350, 400, 450, 500, 550, 600, 650, 700, 750, 800, 850, or 900 mM salt. In some embodiments, the salt selection medium contains any of about 50, 100, 150, 200, 250, 300, or 350 mM to any of about 400, 450, 500, 550, 600, 650, 700, 750, 800, 850, or 900 mM salt.

In some embodiments, osmotic tolerance of a selected mutant is at least about 10%, 20%, 30%, 40%, or 50% higher than the osmotic tolerance of the parent strain from which it was derived (i.e., at least about 10%, 20%, 30%, 40%, or 50% increase in growth and/or viability in an osmotic tolerance test in comparison with the viability of the parent strain under identical conditions). Such mutants may be advantageous in certain fermentation conditions. For example, a strain with increased osmotic tolerance may be more tolerant to high osmotic pressure conditions such as, for example, high sugar concentrations in liquid media or other compositions with high sugar content, such as liquid hydrolysates of biomass, such as cellulosic biomass, for example, lignocellulosic biomass.

Osmotic tolerance may be assessed by determining % viability under osmotic shock conditions (e.g., high salt, sugar, and/or solid concentrations) in comparison to another microbial strain, such as the parent strain. Osmotic shock tolerance and/or membrane fluidity may also be assessed, for example, by determining resistance to osmotic shock using the method described in Dunlap et al. (2007) *FEMS Yeast Res* 7:449-458.

In one embodiment, the method for selecting a microbial strain with increased osmotic tolerance includes: (a) contacting microbial cells with a mutagen to produce mutants; (b) plating the mutants on solid medium in selection plates that contain salt selection medium with a concentration of salt sufficient to inhibit growth of the parent strain by at least about 90, 95, 98, or 99%; (c) incubating the selection plates under conditions suitable for growth of microbial colonies; (d) selecting colonies that grow on the first selection plates; and (e) assessing osmotic tolerance for colonies that grow on the selection plates to identify a microbial strain with greater osmotic shock tolerance than the parent strain from which it was derived. In some embodiments, osmotic tolerance, i.e., growth and/or viability under high osmotic pressure, is at least about 10%, 20%, 30%, 40%, or 50% higher than the parent strain from which it was derived. Optionally, prior to step (e), colonies that grow on the first selection plates (step (d)) may be restreaked on second selection plates that contain salt in a concentration that is substantially the same as the first selection plates, followed by incubation of the second selection plates under conditions suitable for growth of bacterial colonies, and selection of colonies that grow on the second section plates. Colonies that grow on the second selection plates are then assessed for osmotic tolerance to identify strains with higher osmotic tolerance, e.g., at least about 10% higher osmotic tolerance, than the parent strain from which the mutants are derived.

The salt used for the selection may be organic or inorganic, or a combination thereof. Nonlimiting examples of inorganic salts that may be used for the selection method include sodium chloride, potassium chloride, potassium phosphate, ammonium sulfate, calcium chloride, and calcium phosphate, or a mixture thereof. In one embodiment, the salt is sodium chloride. In one embodiment, salt(s) are present in the salt selection medium at a total concentration of about 50 mM to about 500 mM, about 50 mM to about 150 mM, about 100 mM to about 250 mM, about 200 mM to about 400 mM, about 300 mM to about 450 mM, about 400 mM to about 550 mM, or about 100 mM to about 900 mM. In some embodiments, salt(s) are present in the salt selection medium at a total concentration of any of about 50, 100, 150, 200, 250, 300, 350, 400, 450, 500, 550, 600, 650, 700, 750, 800, 850, or 900 mM. In some embodiments, salt(s) are present in the salt selection medium at a concentration of any of about 50, 100, 150, 200, 250, 300, or 350 mM to any of about 400, 450, 500, 550, 600, 650, 700, 750, 800, 850, or 900 mM.

In some embodiments, the salt selection medium is produced by adding salt to a medium that already contains salt(s) and/or inhibitor(s) of microbial growth and/or bioproduct (e.g., solvent) production.

The microbial parent strain may be bacterial or fungal. In one embodiment, the microbial strain is bacterial, for example, selected from the genera *Clostridium, Lactobacillus, Enterococcus, Escherichia, Bacillus, Pichia, Pseudomonas, Synechocystis*, or *Saccharomyces*. In some embodiments, the microbial strain is a *Clostridium* species, for example, *Clostridium acetobutylicum, Clostridium beijerinckii, Clostridium saccharobutylicum, Clostridium puniceum, Clostridium saccharoperbutylacetonicum, Clostridium pasteuranium, Clostridium butylicum, Clostridium aurantibutyricum, Clostridium tetanomorphum, Clostridium thermocellum*, and *Clostridium thermosaccharolyticum*.

In some embodiments, the parent strain from which mutants with higher osmotic tolerance are derived is a strain that produces a bioproduct. Nonlimiting examples of such bioproducts include biochemical or biochemical intermediates, for example, formate, acetate, butyrate, propionate, succinate, methanol, propanol, or hexanol. The bioproduct may optionally be a solvent, for example, a polar aprotic or protic solvent. In some embodiments, the solvent is selected from n-butanol, acetic acid, isopropanol, ethanol, methanol, formic acid, 1,4-dioxane, tetrahydrofuran, acetone, acetonitrile, dimethylformamide, or dimethyl sulfoxide, or a combination thereof. In one embodiment, the solvent is n-butanol. A solvent-producing strain, selected for increased osmotic tolerance as described herein, may also exhibit increased solvent tolerance and/or titer.

In some embodiments, a mutant with increased osmotic tolerance, produced as described herein, also exhibits an increased tolerance to inhibitor(s) of microbial growth and/or bioproduct (e.g., solvent) production that are present in hydrolyzed feedstock, relative to the microbial strain from which it was derived. In some embodiments, the mutant exhibits at least about 10, 20, 30, 40, or 50% improvement in growth in the presence of untreated hydrolyzed feedstock (for example, acid hydrolyzed lignocellulosic feedstock) in comparison with the parent strain from which it was derived). Examples of inhibitors that may be present in hydrolyzed feedstock include, but are not limited to, 5-hydroxyy-methyl furfural (HMF), furfural, aliphatic acids, levulinic acid, acetic acid, formic acid, phenolic compounds, vanillin, dihydroconiferylalcohol, coniferyl aldehyde, vanillic acid, hydroquinone, catechol, acetoguaiacone, vanillic acid, homovanillic acid, vanillin, Hibbert's ketones, ammonium nitrate, p-coumaric acid, ferulic acid, 4-hydroxybenzoic acid, syringaldehyde, galacturonic acid, and glucuronic acid.

In some embodiments, a mutant with increased osmotic tolerance, selected as described herein, produces a bioproduct, and also exhibits an increased tolerance to and/or titer for the bioproduct and/or further exhibits an increased tolerance to inhibitor(s) of microbial growth and/or bioproduct production, such as inhibitor(s) present in hydrolyzed feedstock, as described above. In one embodiment, a mutant with increased osmotic tolerance, selected as described herein, is a solvent producing mutant that also exhibits an increased solvent tolerance and/or titer, and/or further exhibits an increased tolerance to inhibitor(s) of microbial growth and/or solvent production, such as inhibitor(s) present in hydrolyzed feedstock, as described above.

In some embodiments, second or further rounds of selection are performed. For example, a mutant selected for increased osmotic tolerance as described above ("first mutant strain") may be further mutagenized to produce "second mutants." The second mutants are cultured on salt selection medium that may contain the same or different (higher or lower) amount of salt that was added in the first round of selection from which the first mutant strain was selected. Salt may be included in the salt selection medium in an amount sufficient to inhibit growth of the first mutant strain by at least about 90, 95, 98, or 99%. In one embodiment, the salt selection medium for the second round of selection contains more salt than the salt selection medium that was used for selection of the first mutant strain. In some embodiments, about 50 mM more salt is included in the salt selection medium for the second round of selection than was included for the first round of selection. In some embodiments, about 100 mM more salt is included in the salt selection medium for the second round of selection than was included for the first round of selection. Osmotic tolerance is assessed for colonies that grow in the presence of salt, and second mutants are identified that have a higher osmotic tolerance than the first mutant strain. In some embodiments, osmotic tolerance of a second mutant strain is at least about 10% higher than the osmotic tolerance in the first mutant strain from which the second mutant was derived. In some embodiments, second mutant strains are derived from a bioproduct-producing strain and exhibit an increased bioproduct tolerance and/or titer, and or an increased tolerance to inhibitor(s) of microbial growth and/or bioproduct product, such as inhibitor(s) present in hydrolyzed feedstock, relative to the first mutant strain, in addition to increased osmotic tolerance. In one embodiment, second mutant strains are derived from a solvent-producing strain and exhibit an increased solvent tolerance and/or titer, and/or an increased tolerance to inhibitor(s) of microbial growth and/or solvent production, such as inhibitor(s) that are present in hydrolyzed feedstock, relative to the first mutant strain, in addition to increased osmotic tolerance. One or more further rounds of selection (third, fourth, fifth, etc.) may be performed if desired to obtain strains with further improved osmotic tolerance, bioproduct (e.g., solvent) tolerance, bioproduct (e.g., solvent) titer, and/or tolerance to inhibitor(s), such as inhibitor(s) present in hydrolyzed feedstock.

Microbial Strains

Microbial strains are provided that have been selected for increased bioproduct (e.g., solvent) tolerance and/or bioproduct (e.g., solvent) titer and/or osmotic tolerance by any of the methods described herein. In some embodiments, a microbial strain selected by any of the methods described herein also has an increased tolerance to one or more inhibitor(s) of microbial growth and/or bioproduct (e.g., solvent) production, such as inhibitor(s) present in hydrolyzed feedstock.

In one embodiment, a microbial strain is provided that has tolerance to a bioproduct that is produced by and is toxic to the cells that is at least about 5%, 10%, 20%, 25%, 30%, 40%, 50%, 60%, 70%, 80%, 90%, or 100% higher than the bioproduct tolerance in the parent strain from which it was derived. In one embodiment, bioproduct tolerance of the microbial strain is about 5% to about 100% higher than the bioproduct tolerance in the parent strain from which it was derived. In some embodiments, the bioproduct tolerance is any of about 5%, 10%, 20%, 25%, 30%, or 40% to any of about 50%, 60%, 70%, 80%, 90%, or 100% higher in the microbial strain than the parent strain from which it was derived. In some embodiments, the microbial strain with increased bioproduct tolerance also exhibits an increased bioproduct titer and/or an increased osmotic tolerance and/or an increased tolerance to inhibitor(s) of microbial growth and/or bioproduct production, such as inhibitor(s) present in hydrolyzed feedstock, relative to the parent strain from which it was derived.

In one embodiment, a microbial strain is provided that has a solvent tolerance that is at least about 5%, 10%, 20%, 25%, 30%, 40%, 50%, 60%, 70%, 80%, 90%, or 100% higher than the solvent tolerance in the parent strain from which it was derived. In one embodiment, solvent tolerance of the microbial strain is about 5% to about 100% higher than the solvent tolerance in the parent strain from which it was derived. In some embodiments, the solvent tolerance is any of about 5%, 10%, 20%, 25%, 30%, or 40% to any of about 50%, 60%, 70%, 80%, 90%, or 100% higher in the microbial strain than the parent strain from which it was derived. In some embodiments, the microbial strain with increased solvent tolerance also exhibits an increased solvent titer and/or an increased osmotic tolerance and/or an increased tolerance to inhibitor(s) of microbial growth and/or solvent production, such as inhibitor(s) present in hydrolyzed feedstock, relative to the parent strain from which it was derived.

In one embodiment, a microbial strain is provided that exhibits a bioproduct titer that is at least about 5%, 10%, 25%, 50%, 75%, 100%, 125%, 150%, 175%, or 200% higher in the microbial strain than the parent strain from which it was derived. In one embodiment, the titer is about 5% to about 200% higher in the microbial strain than the parent strain from which it was derived. In some embodiments, the titer is any of about 5%, 10%, 25%, 50%, or 75% to any of about 100%, 125%, 150%, 175%, or 200% higher in the microbial strain mutant than the parent strain from which it was derived. In some embodiments, the microbial strain with increased bioproduct titer also exhibits increased bioproduct tolerance and/or increased osmotic tolerance and/or an increased tolerance to inhibitor(s) of microbial growth and/or bioproduct production, such as inhibitor(s) present in hydrolyzed feedstock, relative to the parent strain from which it was derived.

In one embodiment, a microbial strain is provided that exhibits a solvent titer that is at least about 5%, 10%, 25%, 50%, 75%, 100%, 125%, 150%, 175%, or 200% higher in the microbial strain than the parent strain from which it was derived. In one embodiment, the titer is about 5% to about 200% higher in the microbial strain than the parent strain from which it was derived. In some embodiments, the titer is any of about 5%, 10%, 25%, 50%, or 75% to any of about 100%, 125%, 150%, 175%, or 200% higher in the microbial strain mutant than the parent strain from which it was derived. In some embodiments, the microbial strain with increased solvent titer also exhibits increased solvent tolerance and/or increased osmotic tolerance and/or an increased tolerance to inhibitor(s) of microbial growth and/or solvent production, such as inhibitor(s) present in hydrolyzed feedstock, relative to the parent strain from which it was derived.

In one embodiment, a microbial strain is provided that exhibits at least about 10%, 20%, 30%, 40%, or 50% higher osmotic tolerance than the parent strain from which it was derived. In some embodiments, the microbial strain with increased osmotic tolerance also exhibits increased tolerance to a bioproduct that is produced by and is toxic to the cells and/or a higher bioproduct titer, and/or a increased tolerance to inhibitor(s) of microbial growth and/or bioproduct production, such as inhibitor(s) present in hydrolyzed feedstock, relative to the parent strain from which it was derived. In one embodiment, the microbial strain is derived from a solvent-producing strain and produces a solvent, and exhibits increased solvent tolerance and/or increased solvent titer and/or increased tolerance to inhibitor(s) of microbial growth and/or solvent production, such as inhibitor(s) present in hydrolyzed feedstock, relative to the solvent-producing parent strain from which it was derived.

In some embodiments, a microbial strain with increased bioproduct (e.g., solvent) tolerance and/or bioproduct (e.g., solvent) titer and/or osmotic tolerance produced by any of the methods described herein exhibits an increased survival when exposed to a mutagenic compound, in comparison to the parent strain from which it was derived. In one embodiment, the mutagen causes base pair substitutions. In some embodiments, the mutagenic compound is selected from ethyl methane sulfonate (EMS) and N-methyl-N'-nitro-N-nitrosoguanidine (MNNG). In one embodiment, the mutagenic compound is EMS and the microbial strain exhibits at least about 10% higher survival than the parent strain from which is was derived. In one embodiment, the mutagenic compound is MNNG and the microbial strain exhibits at least about 80% higher survival than the parent strain from which it was derived.

In some embodiments, a microbial strain with increased bioproduct (e.g., solvent) tolerance and/or bioproduct (e.g., solvent) titer and/or osmotic tolerance produced by any of the methods described herein exhibits an altered morphology in comparison with the parent strain from which it was derived. In some embodiments, the cell membrane of the microbial cells visually or microscopically appears less rigid and/or more fluid. This is surprising because it has been hypothesized that greater membrane fluidity in *Clostridium acetobutylicum* correlates with decreased butanol tolerance. (See Vollherbst-Schneck et al. (1984) *Appl Environ Microbiol* 47:193-194; Baer et al. (1987) *Appl Environ Microbiol* 53:2854-2861.) In other embodiments, the cell membrane of the microbial cells visually or microscopically appears more rigid and/or less fluid than the membrane of the parent (e.g., solvent-producing) strain from which it was derived.

In some embodiments, a microbial cell selected by any of the methods described herein produces a bioproduct at a higher yield and/or productivity than the parent cell from which it was derived. The microbial cell may be a solvent-producing cell, and may produce a solvent at a higher yield and/or productivity in comparison with the solvent-producing parent cell from which it was derived. In some embodiments, the microbial cell is selected for increased solvent tolerance and/or solvent titer and produces a solvent at a higher yield and/or productivity than the parent cell from which it was derived.

Methods for Producing a Bioproduct

Methods for producing a bioproduct, e.g., a solvent, are provided. One or more microbial strain(s) selected for increased bioproduct (e.g., solvent) tolerance and/or increased bioproduct (e.g., solvent) titer and/or increased osmotic tolerance by any of the methods described herein may be cultured in a bioreactor under conditions suitable for bioproduct, e.g., solvent production, and the bioproduct, e.g., solvent, that is produced may be recovered and/or purified from the fermentation broth in which the microbial strain is cultured.

In some embodiments, the microbial strain is immobilized on a solid support in a bioreactor. In some embodiments, the immobilized microbial strain is in the form of a biofilm.

Feedstock

A feedstock is a substance that provides the base material from which sugar molecules are generated for inclusion in a microbial growth medium, to support the growth of the microorganism. In some embodiments, the feedstock is cellulosic biomass, for example, lignocellulosic biomass. Any material containing cellulose and/or hemicellulose may be used as the feedstock. The material may contain cellulose and/or hemicellulose without lignin.

In some embodiments, the feedstock is woody biomass. In one embodiment, the feedstock is softwood, for example, pine, e.g., Lodgepole pine. In another embodiment, the feedstock is hardwood, for example, maple, birch, or ash. In another embodiment, the feedstock is mixed hardwood and softwood. In another embodiment, the feedstock is mixed hardwood. In some embodiments, the woody biomass is in the form of wood chips, sawdust, saw mill residue, or a combination thereof.

Lignocellulose contains a mixture of carbohydrate polymers and non-carbohydrate compounds. The carbohydrate polymers contain cellulose and hemicellulose, and the non-carbohydrate portion contains lignin. The non-carbohydrate portion may also contain ash, extractives, and/or other components. The specific amounts of cellulose, hemicelluloses, and lignin depends on the source of the biomass. For example, municipal solid waste may contain primarily cellulose, and extract streams from a paper and pulp plant may contain primarily hemicelluloses. The remaining composition of lignocelluloses may also contain other compounds such as proteins.

Cellulose, which is a β-glucan built up of D-glucose units linked by β(1,4)-glycosidic bonds, is the main structural component of plant cell walls and typically constitutes about 35-60% by weight (% w/w) of lignocellulosic materials.

Hemicellulose refers to non-cellulosic polysaccharides associated with cellulose in plant tissues. Hemicellulose frequently constitutes about 20-35% w/w of lignocellulosic materials, and the majority of hemicelluloses consist of polymers based on pentose (five-carbon) sugar units, such as D-xylose and D-arabinose units, hexose (six-carbon) sugar units, such as D-glucose and D-mannose units, and uronic acids such as D-glucuronic acid.

Lignin, which is a complex, cross-linked polymer based on variously substituted p-hydroxyphenylpropane units, typically constitutes about 10-30% w/w of lignocellulosic materials.

Lignocellulosic biomass may be derived from a fibrous biological material such as wood or fibrous plants. Examples of suitable types of wood include, but are not limited to, spruce, pine, hemlock, fir, birch, aspen, maple, poplar, alder, *salix*, cottonwood, rubber tree, marantii, eucalyptus, sugi, and acase. Examples of suitable fibrous plants include, but are not limited to, corn stover and fiber, flax, hemp, *cannabis*, sisal hemp, bagasse, straw, cereal straws, reed, bamboo, mischantus, kenaf, canary reed, *Phalaris arundinacea*, and grasses. Other lignocellulosic materials may be used such as herbaceous material, agricultural crop or plant residue, forestry residue, municipal solid waste, pulp or paper mill residue, waste paper, recycling paper, or construction debris. Examples of suitable plant residues include, but are not limited to, stems, leaves, hulls, husks, cobs, branches, bagasse, wood chips, wood pulp, wood pulp, and sawdust. Examples of suitable waste paper include, but are not limited to, discarded paper of any type (e.g., photocopy paper, computer printer paper, notebook paper, notepad paper, typewriter paper), newspaper, magazines, cardboard, and paper-based packaging material.

Other feedstocks that may be used in the bioproduct, e.g., solvent, production processes described herein include hemicellulose extract from wood, beet extract, beet molasses, sorghum syrup, barley hulls, potato processing waste, and brewers mash.

In some embodiments, a feedstock mix containing about 40% logging residues, about 20% sustainable roundwood, about 20% woody energy crops, and about 20% herbaceous energy crops may be used. This blend can account for regional variation and provide significant flexibility in selecting locations for facilities and in procuring feedstock supply contracts.

Feedstock flexibility may permit utilization of combinations of feedstocks in geographic locations where the available supply of feedstocks taken individually are not sufficient to justify a commercial scale biobutanol production plant, or where synergistic value can be realized from combining feedstocks that allow for better practices to be implemented with regard to the underlying land (e.g., improved crop rotations) or in terms of more economic harvest, handling and storage logistics. Feedstock flexibility may also provide opportunities to locate plants in niche sites where end use markets are in close proximity to otherwise non-utilizable feedstocks.

In some embodiments, diverse feedstocks may be utilized by versatile strains that are capable of converting both 5-carbon and 6-carbon sugar molecules (including multimeric forms) to a bioproduct, such as a solvent, for example, n-butanol. In some embodiments, a feedstock may be hydrolyzed to provide hydrolysates that are rich in 5-carbon or 6-carbon sugars, and microbial strains which have been optimized for growth and bioproduct (e.g., solvent) production on 5-carbon or 6-carbon sugars are used as parent strains for production of mutants as described herein, either in separate or combined fermentations. In some embodiments, a microbial strain that has been optimized for growth on a particular feedstock or hydrolysate generated from a particular feedstock, is used as the parent strain.

Pretreatment of Feedstock

Feedstocks such as those described herein can be pretreated using a variety of methods and systems prior to bioconversion. Preparation of the feedstock can include chemical or physical modification of the feedstock. For example, the feedstock can be shredded, sliced, chipped, chopped, heated, burned, dried, separated, extracted, hydrolyzed, and/or degraded. These modifications can be performed by biological, non-biological, chemical, or non-chemical processes.

In some embodiments in which a cellulosic, e.g., lignocellulosic, feedstock is used, processes may be used to break down cellulose and/or hemicellulose into sugar molecules that may be more easily processed by a microorganism. Processes that may be used include acid hydrolysis, enzymatic hydrolysis, gasification, pyrolysis, and cellulose degradation by a microorganism.

Deconstruction

In some embodiments, the feedstock, such as lignocellulosic feedstock, for example, wood chips, sawdust, and/or sawdust residue, is deconstructed prior to a downstream pretreatment process such as hydrolysis. Deconstruction may include, but is not limited to, presteaming to swell and loosen material, mechanical grinding, mechanical explosion (e.g., steam or other chemical treatment followed by rapid decompression), vacuum treatment, acid-feedstock contact (diffusion of acid into feedstock), or a combination thereof. In some embodiments, deconstruction renders cellulose and/or hemicellulose in the feedstock more accessible for hydrolysis.

Removal of Extractives

In some embodiments, the feedstock, such as lignocellulosic feedstock, for example, wood chips, sawdust, and/or sawdust residue, is pretreated to remove extractives. Extractives are material that is extracted from the feedstock by a process such as compression, water or solvent extraction, or air drying. Non-limiting examples of extractives include terpenes, resin acids, fatty acids, sterols, phenolic compounds, and triglycerides. Extractives may include, but are not limited to, p-coumaric acid, ferulic acid, 4-hydroxybenzoic acid, vanillic acid, syringaldehyde, vanillin, furfural, hydroxymethylfurfural, and glucuronic acid. Extractives may be removed for other uses, such as production of sterols, or burned to provide energy.

In some embodiments, extractives are removed prior to or in conjunction with deconstruction of the feedstock.

Hydrolysis

Typically, a feedstock contains sugar molecules in an oligomeric form, e.g., a polymeric form, and must be hydrolyzed to extract and release soluble monomeric and/or multimeric sugar molecules, which are converted to a bioproduct, such as a solvent, in a microbial fermentation as described herein. In some embodiments, the sugar molecules are present in the feedstock in cellulose and/or hemicellulose. In one embodiment, the feedstock is lignocellulosic biomass and the sugar molecules are present in the feedstock in cellulose and hemicelluloses.

In some embodiments, the feedstock is pretreated with an acid hydrolysis process. Acids that may be used for hydrolysis include, but are not limited to, nitric acid, formic acid, acetic acid, phosphoric acid, and sulfuric acid. In one embodiment, acid hydrolysis is performed in a single stage. In some embodiments, acid hydrolysis is performed in two or more stages, under different conditions in each stage to hydrolyze different components of the feedstock in each stage An acid hydrolysis system may be designed to submerge and flood the feedstock with the acid solution in the hydrolysis reactor, e.g., in a vertical section of the hydrolysis reactor, to insure even acid impregnation. Even heat distribution may be obtained by using both direct steam injection and a jacketed vessel in conjunction with a mechanical screw auger. Variable speed drives may be used with temperature sensing instrumentation to control reactor residence time and temperature allowing reactor severity to be adjusted on-line. Alternative reactor configurations with functionally similar properties may also be utilized.

In some embodiments, a multiple-stage dilute nitric acid hydrolysis process is used. In one embodiment, a two-stage dilute nitric acid process is used. In one embodiment, conditions in the first stage are chosen to achieve hydrolysis of about 70% to about 90% of the hemicellulose in the feedstock and conditions in the second stage are chosen to achieve hydrolysis of about 40% to about 70% of the cellulose in the feedstock. The first stage mainly targets the hydrolysis of the hemicellulose, yielding a mannose and/or xylose rich hydrolysate, whereas the second stage uses the solids remaining from the first stage and targets the cellulose, yielding a glucose rich hydrolysate. Typically, first stage hydrolysate liquors contain a mix of 5-carbon and 6-carbon sugars, and second stage hydrolysate contains primarily 6-carbon sugars, in both cases as soluble monomeric and/or multimeric forms. 6-carbon monosaccharides may include, but are not limited to, glucose, mannose, and galactose. 6-carbon disaccharides may include, but are not limited to, cellobiose, mannobiose, glucomannose, and galactomannose. Other multimeric forms may include, but are not limited to, cellotriose, cellotetrose, and cellopentose. 5-carbon monosaccharides may include, but are not limited to xylose and arabinose. 5-carbon disaccharides may include, but are not limited to, xylobiose, xylotriose, and arabinoxylose.

In some embodiments in which hardwood is used as the feedstock, the first stage hydrolysate contains about 60% to about 75% 5-carbon sugar by weight and about 25% to about 40% 6-carbon sugar by weight, and the second stage hydrolysate contains about 80% to about 95% 6-carbon sugar by weight. In some embodiments in which softwood is used as the feedstock, the first stage hydrolysate contains about 20% to about 30% 5-carbon sugar by weight and about 70% to about 80% 6-carbon sugar by weight, and the second stage hydrolysate contains about 90% to about 100% 6-carbon sugar by weight, wherein the second stage is performed at a higher temperature than the first stage.

A first stage hydrolysis module may be coupled to a second stage hydrolysis module, with solid residue separated from liquid hydrolysate generated in the first stage hydrolysis serving as substrate for the second hydrolysis process.

In some embodiments, the second stage hydrolysis is performed at a higher temperature than the first stage hydrolysis. In some embodiments, hydrolysis is performed at a nitric acid concentration of about 1% to about 4%, about 1.3% to about 3.5%, or about 1.3% (w/w of dry feedstock) for both hydrolysis stages, at a temperature of about 170° to about 175° C. in the first stage and a temperature of about 210° to about 230° C. in the second stage, and at the saturation pressure for steam at the reactor temperature for each hydrolysis stage.

In some embodiments, the liquid (acid) to solid (feedstock) ratio for hydrolysis is about 10:1 to about 5:1 or about 7.5:1 to about 5:1. In a circulating reactor, the ratio of liquid to solid may be about 5:1 to about 3:1 or about 3.5:1 to about 3:1. In a continuous extrusion reactor, the ratio of liquid to solid may be about 4:1 to about 0.5:1.

In some embodiments, the soluble sugar extraction yield from the feedstock in the first stage hydrolysis as about or at least about 6, 10, 15, 20, 30, 34, 40, 50, or 60% from cellulose and about or at least about 1, 3, 6, 10, 20, 40, 60, 70, 75, 80, 85, 90, 95, or 99% from hemicellulose. In some embodiments, the soluble sugar extraction yield from solid residue remaining after the first stage hydrolysate in the second stage hydrolysis is about or at least about 25, 35, 45, 55, 65, 75, 85, or 95% from cellulose and about or at least about 1, 3, 6, or 10% from hemicellulose.

In some embodiments, conditions are chosen such that short residence times may be utilized, providing high productivity (smaller reactors) and minimal sugar degradation products. Minimizing degradation products makes the pretreatment step more compatible with the downstream fermentation process. For example, in some embodiments, residence time in the hydrolysis reactor for first stage nitric acid hydrolysis with ¼ inch wood chips may be about 5 to about 8 minutes, with longer residence time of about 1 to about 30 minutes for larger feed material, and residence time for ¼ inch wood chips for second stage nitric acid hydrolysis may be about 3 to about 6 minutes, with longer residence time for larger feed material.

Dilute nitric acid pretreatment has several advantages over other types of acid pretreatment. The passivation characteristics of nitric acid at lignocellulosic pretreatment conditions permit the use of stainless steel, rather than the more exotic and expensive materials required for other pretreatment processes, such as dilute sulfuric acid treatment. This confers a substantial capital cost advantage. Further, the hydrolysis and neutralization process is rich in nitrogen that can be utilized in fermentation. In some embodiments, hydrolysate streams are neutralized with ammonia to produce ammonium nitrate Ammonium nitrate is a nutrient for microorganisms in the downstream fermentation process.

Parameters for nitric acid hydrolysis of feedstock are also described in U.S. Pat. Nos. 4,384,897, 4,706,903, 5,221,357, 5,366,558, 5,536,325, 5,628,830, and 6,019,900.

In a multiple-stage hydrolysis process as described herein, hydrolysis reactors for each stage may be the same or different. For example, a second stage reactor may have a higher or lower capacity than a first stage reactor. In some embodiments, a hydrolysis reactor may have an internal volume of about or at least about 1, 2, 5, 10, 20, 50, 100, 200, 500, 1000, 2500, or 5000 gallons. In some embodiments, a nitric acid hydrolysis reactor may be smaller than a comparable capacity sulfuric acid hydrolysis reactor.

In a multiple-stage hydrolysis process as described herein, such as a two-stage nitric acid hydrolysis process, one or more processing operations can be used between stages, such as between first and second nitric acid hydrolysis stages, including mechanical degradation, drying, shaking mixing, chipping, straining, solid-liquid, liquid-liquid, or gas-liquid separation phase separation, decanting, and shearing. Such operations may be used for separation, degradation, attrition, or shearing of an input material.

In some embodiments, a hydrolysis system can include a steam compressor to compress low pressure flash steam. In some embodiments, low pressure flash steam from the first and/or second stage of a nitric acid hydrolysis process may be compressed. By raising the pressure, the low pressure flash steam can be re-used in downstream product concentration and/or product distillation operations and significantly reduce the energy requirements of the overall process.

A hydrolysis system for use in the processes described herein can be optimized to produce the greatest yield of products per amount of feedstock, energy required, greenhouse gas emitted, or any combination thereof. Optimization parameters include the type of separations or reactions performed outside of the hydrolysis reactors, and the conditions of the hydrolysis reactors. In some embodiments, degradation and/or hydrolysis of the feedstock material may be reduced or increased due to impact on energy consumption or product yield.

In bioproduct, e.g., solvent production processes and systems described herein, a feedstock hydrolysis process as described herein and a fermentation process are coupled to process feedstock in a continuous manner. The continuous operation may be designed such that accumulation of materials between the hydrolysis unit and fermentor is avoided. In some embodiments, a hydrolysis unit may be operated continuously for about or at least about 50, 100, 200, 300, 400, 600, 800, 1000, 1350, 1600, 2000, 2500, 3000, 4000, 5000, or 6000 hours.

Lignin-containing solid residue remaining after hydrolysis of a lignocellulosic feedstock may be used as an energy source for the bioproduct, e.g., solvent, production process described herein and/or as a fuel source for electricity generation. In some embodiments, lignin-containing residue is dried to a liquid content of about 15% or less and the dried residue may be burned as a fuel source for energy or electricity generation, gasified for subsequent combustion or conversion to other chemical products, or converted to other chemical products.

Conditioning of Hydrolyzed Feedstock

In some embodiments, hydrolyzed feedstock is "conditioned" to remove inhibitors of microbial growth and/or bioproduct, e.g., solvent, production, prior to addition of the hydrolyzed feedstock to microbial growth medium. Such inhibitors may include, but are not limited to, organic acids, furans, phenols, soluble lignocellulosic materials, extractives, and ketones. Inhibitors present in wood hydrolysates may include, but are not limited to, 5-hydroxyy-methyl furfural (HMF), furfural, aliphatic acids, levulinic acid, acetic acid, formic acid, phenolic compounds, vanillin, dihydroconiferylalcohol, coniferyl aldehyde, vanillic acid, hydroquinone, catechol, acetoguaiacone, homovanillic acid, 4-hydroxy-benzoic acid, Hibbert's ketones, ammonium nitrate, p-coumaric acid, ferulic acid, 4-hydroxybenzoic acid, vanillic acid, syringaldehyde, and glucuronic acid.

Nonlimiting examples of conditioning processes include vacuum or thermal evaporation, overliming, precipitation, adsorption, enzymatic conditioning (e.g., peroxidase, laccase), chemical conversion, distillation, and ion exchange. In one embodiment, conditioning includes contact of hydrolyzed feedstock with an ion exchange resin, such as an anion or cation exchange resin. Inhibitors may be retained on the resin. In one embodiment, the ion exchange resin is an anion exchange resin. Ion exchange resins may be regenerated with caustic, some solvents, potentially including those generated in a solvent production process described herein, or other known industrial materials.

In some embodiments, microbial growth and/or bioproduct (e.g., solvent) titer, yield, and/or productivity is increased when conditioned hydrolyzed feedstock is used, in comparison to identical hydrolyzed feedstock which has not been subjected to the conditioning process.

In one embodiment, an extractive removal process, as described supra, is used instead of a conditioning process to improved microbial growth and/or bioproduct (e.g., solvent) titer, yield, and/or productivity. In one embodiment, an extractive removal process, as described supra, is used in addition to a conditioning process to improve microbial growth and/or bioproduct (e.g., solvent) titer, yield, and/or productivity. An extractive removal process may also be used in some embodiments to generate an additional stream to provide products with commercial value (e.g., sterols) and/or to improve operational parameters (e.g., less resin and regenerant to regenerate the resin (e.g., caustic) required for removal of fermentation and/or bioproduct (e.g., solvent) production inhibitors).

Fermentation

In some embodiments, the bioproduct, e.g., solvent, production process herein includes fermentation of a bioproduct-producing, e.g., solvent-producing, microorganism in an immobilized cell bioreactor (i.e., a bioreactor containing cells that are immobilized on a support, e.g., a solid support). In some embodiments, an immobilized cell bioreactor provides higher productivity due to the accumulation of increased productive cell mass within the bioreactor compared with a stirred tank (suspended cell) bioreactor. In some embodiments, the microbial cells form a biofilm on the support and/or between support particles in the growth medium.

In some embodiments, the bioproduct, e.g., solvent, production process herein includes continuous fermentation of a microorganism (continuous addition of feedstock (e.g., hydrolyzed feedstock) and withdrawal of product stream). Continuous fermentation minimizes the unproductive portions of the fermentation cycle, such as lag, growth, and turnaround time, thereby reducing capital cost, and reduces the number of inoculation events, thus minimizing operational costs and risk associated with human and process error.

Fermentation may be aerobic or anaerobic, depending on the requirements of the bioproduct-producing, e.g., solvent-producing microorganism.

In some embodiments, an immobilized bioproduct-producing, e.g., solvent-producing, *Clostridium* strain is fermented anaerobically in a continuous process as described herein. In one embodiment, the support is bone char.

One or more bioreactors may be used in the bioproduct, e.g., solvent, production systems and processes described herein. When multiple bioreactors are used they can be arranged in series and/or in parallel. The advantages of multiple bioreactors over one large bioreactor include lower fabrication and installation costs, ease of scale-up production, and greater production flexibility. For example individual bioreactors may be taken off-line for maintenance, cleaning, sterilization, and the like without appreciably impacting the production schedule. In embodiments in which multiple bioreactors are used, the bioreactors may be run under the same or different conditions.

In a parallel bioreactor arrangement, hydrolyzed feedstock is fed into multiple bioreactors, and effluent from the bioreactors is removed. The effluent may be combined from multiple bioreactors for recovery of the bioproduct, e.g., solvent, or the effluent from each bioreactor may be collected separately and used for recovery of the bioproduct, e.g., solvent.

In a series bioreactor arrangement, hydrolyzed feedstock is fed into the first bioreactor in the series, the effluent from the first bioreactor is fed into a second downstream bioreactor, and the effluent from each bioreactor in the series is fed into the next subsequent bioreactor in the series. The effluent from the final bioreactor in the series is collected and may be used for recovery of the bioproduct, e.g., solvent.

Each bioreactor in a multiple bioreactor arrangement can have the same species, strain, or mix of species or strains of microorganisms or a different species, strain, or mix of species or strains of microorganisms compared to other bioreactors in the series.

In some embodiments, feedstock is hydrolyzed in a multistage process as described herein, and hydrolysate from each stage is fed to a separate bioreactor. The bioreactors to which the different hydrolysates are fed may contain the same or different microbial species or strains. In one embodiment, the bioreactors to which the different hydrolysates are fed contain different microbial species or strains that have each been optimized for growth on the particular hydrolysate being fed to that bioreactor. In some embodiments, different sets of multiple bioreactors in series are fed hydrolysate from different stages of hydrolysis of the feedstock.

In some embodiments, effluent can be recycled after the harvesting of bioproduct, e.g., solvent, and used to make the initial fermentation media or a feed stream for future fermentations, thereby allowing maximum utilization of unassimilated and recovered nutrients and minerals. In some embodiments, product is isolated from the effluent and the product reduced effluent is then used as a feedstock for the next bioreactor in the series.

The order of bioreactors in a series can be adjusted to prevent or remove blockage due to excessive microbial growth. For example, when the first fermentor in a series reaches a high level of cell mass, it can be placed second in the series to instead receive effluent with high product concentration or reduced nutrient levels that may inhibit further cell growth. The timely shifting of the order of fermentors may prevent cell overgrowth and blockage of the bioreactor.

Immobilized cell bioreactors allow higher concentrations of productive cell mass to accumulate and therefore, the bioreactors can be run at high dilution rates, resulting in a significant improvement in volumetric productivity relative to cultures of suspended cells. Since a high density, steady state culture can be maintained through continuous culturing, with the attendant removal of product containing fermentation broth, smaller capacity bioreactors can be used. Bioreactors for the continuous fermentation of *C. acetobutylicum* are known in the art. (U.S. Pat. Nos. 4,424,275, and 4,568,643.)

Bioreactors for use in bioproduct, e.g., solvent, production processes and systems herein may be designed for continuous operation for at least about 100, 250, 300, 500, 750, 1,000, 1250, 1,500, 2,000, 2,250, 2,500, 3,000, 4,000, 5,000 or 6,000 hours.

Bioreactor capacities contemplated for use in the bioproduct, e.g., solvent, production systems herein may have a capacity (total nominal volume) of about or at least about 100 L, 1000 L, 6,000 L, 10,000 L, 46,000 L, 50,000 L, 100,000 L, 250,000 L, 270,000 L, or 500,000 L.

Numerous methods of fermentor inoculation are possible including addition of a liquid seed culture to the bottom or the top of the bioreactor and recirculation of the media to encourage growth throughout the bed. Other methods include the addition of a liquid seed culture or impregnated solid support through a port located along the reactor's wall or integrated and loaded with the solid support material. Bioreactor effluent may also be used to inoculate an additional bioreactor and in this case any residual fermentable materials may be converted in the secondary reactor, increasing yield/recovery.

In a similar manner, support material may be added to the reactor through bottom, top, or side loading to replenish support material that becomes degraded or lost from the bioreactor.

Mixing of the bioreactor contents can be achieved through the sparging of sterile gas, e.g., carbon dioxide or $N_2$, which may also serve to prevent contamination of the culture through the maintenance of positive pressure within the fermentor. The evolved gas ($CO_2$, $H_2$) from the fermentation may also be recovered and compressed for utilization in a gas lift or other type reactor to maintain anaerobic, pressurized, well mixed conditions. Other techniques of mixing culture contents include the use of agitators or the recirculation of fermentation broth, particularly broth returned to the bioreactor after the removal of a fermentation product. In some embodiments, the contents of the bioreactor are not mixed, but may rely on the production and movement of evolved gases to mix contents.

In some embodiments of the bioproduct, e.g., solvent, production processes and systems herein, immobilized microorganisms are cultured in packed bed bioreactors, also known as plug-flow bioreactors. In other embodiments, the microorganisms are cultured in expanded bed bioreactors. In other embodiments, the microorganisms are cultured in fluidized bed bioreactors. In still further embodiments, the microorganisms are cultured in bioreactors that are designed to operate in "dual mode," i.e., the bioreactors are capable of operating in either packed bed or expanded/fluidized bed mode. Immobilized cell bioreactors use relatively small sized solid or semi-solid supports that provide a large surface area relative to the volume of the particles, allowing for the microorganisms immobilized on the particles to process large volumes of fluid.

In "packed bed" bioreactors, cells are immobilized on or in semi-solid or solid particles which, due to particle size, mechanical restraint and/or low fluid flow rates do not cause or allow for appreciable axial movement of the supporting material.

In contrast, fluidized and expanded bed reactors use semi-solid or solid support that is not substantially restrained mechanically so that with sufficient fluid flow, usually an upward-flowing stream, the particles become suspended in the stream or "fluidized," i.e., act as if they are part of the fluid stream. The initial seed support particles may become covered by a biofilm over time and can become fully encapsulated by the biofilm. In some cases, agglomeration of cellular mass may lead to suspended biofilm particles in which there is no "seed" purposefully introduced. Fluid drag on the particles is the primary suspension mechanism, but buoyancy forces can also contribute to the suspension of the particles. Typically, the bioreactors use vertical fluid motion to suspend the particles, but other fluid motion is possible including fluid flow at a direction perpendicular to the vertical axis of the bioreactor. The fluid velocity should be sufficient to suspend the particles, but not large enough to carry them out of the vessel. The fluidization of the bed allows the solid particles to move around the bioreactor, causing the fluid within the bioreactor to thoroughly mix. The magnitude of mixing depends on the extent of particle fluidization achieved in the bioreactor. Fluidized and expanded bed bioreactors require relatively larger amounts of energy to operate compared to packed beds because of the volume of fluid that must be circulated to keep the particles suspended.

A "fluidized bed" bioreactor contains support particles with immobilized microorganisms fluidized throughout the full volume of the bioreactor. Particles exit the bioreactor through the outflow and have to be separated from the effluent liquid and returned to the bioreactor. Support material can be removed and recovered from the effluent stream through the use of settling tanks, centrifuges, hydrocyclones, filters (e.g., rotary drum), filter aids, dryers, or distillation apparatus.

An "expanded bed" bioreactor contains support particles with immobilized microorganisms fluidized in the bioreactor, but the bioreactor is designed such that the particles are retained in the bioreactor and do not exit through the outflow. An expanded bed bioreactor contains a particle disengagement zone for separating the fluidized particles from the fluid, thereby retaining the particles within the bioreactor. In some embodiments, separation of the particles from the fluid includes slowing the velocity of the fluid. In some embodiments, this is accomplished by increasing the cross sectional area of the bioreactor. As the fluid velocity slows, the particles start to settle out of the fluid. The top section of the particle disengagement zone is free of particles. An outlet can be located at this top portion to remove effluent. In some embodiments, particles are retained by including filters or screens within the bioreactor.

A dual mode, packed bed-fluidized or expanded bed bioreactor allows for the option of conducting fermentations in either mode for the course of a whole fermentation run. Alternately, the fermentation can alternate between modes during the course of a single fermentation. Dual mode bioreactors can have reduced energy usage compared to conventional fluidized or expanded bed bioreactors because fluidization with its requisite increased energy requirement need only be performed, for example, at relatively high cell densities, high product concentrations, or when pH or nutrient inhomogeneities develop that can be corrected through increased mixing of the bioreactor contents.

In various embodiments, a bioreactor may be configured in a vertical, horizontal, or inclined configuration, to maximize gas/liquid separation and/or to improve elution of evolved fermentation gas to improve overall operation and metrics for the production process, e.g., titer, productivity, and/or yield of bioproduct, e.g., solvent. In one embodiment, a bioreactor may be configured as a "trickle bed reactor," in which the material to be reacted is fed into the bed by a slow flow.

In some embodiments, the amount of a bioproduct, such as a solvent, e.g., butanol, produced per amount of sugar fed to a bioreactor may be about or at least about 0.1, 0.15, 0.2 0.25, 0.3, 0.33, 0.35, 0.4, 0.45, or 0.5 grams per gram sugar converted. In some embodiments, the fermentation may utilize about or at least about 40, 50, 60, 65, 70, 75, 85, or 95% of the available sugar. In some embodiments, about or at least about 20, 30, 40, 50, 60, 70, or 80 gallons of solvent, e.g., butanol, is produced per tonne of feedstock.

In some embodiments, butanol is produced at a productivity of about or at least about 1, 2, 3, 5, 6, 7, 8, 9, 10, 12, 15, 20, 25, 30, 35, 40, 45, or 50 g/L/h.

In some embodiments, bioreactor volumetric productivity and bioproduct, e.g., solvent, for example, butanol, titer may be improved by reducing the particle size of the immobilized support, which can increase available surface area for cell growth, resulting in higher bioreactor productivity. By fluidizing the solid support in fluidized or expanded bed mode, and by using smaller particles with greater size uniformity, mixing can be greatly improved, permitting optimization of nutrients and pH, further improving fermentation performance.

Fermentation Media

Fermentation media for the production of bioproduct, e.g., solvent, products contain feedstock, e.g., a hydrolyzed feedstock, as described herein, as a source of fermentable carbohydrate molecules.

As known in the art, in addition to an appropriate carbon source, fermentation media must contain suitable nitrogen source(s), mineral salts, cofactors, buffers, and other components suitable for the growth of the cultures and promotion of the enzymatic pathway necessary for the production of the desired bioproduct, e.g., solvent. In some embodiments, salts and/or vitamin B12 or precursors thereof are included in the fermentation media. In some cases, hydrolyzed feedstock may contain some or all of the nutrients required for growth, minimizing or obviating the need for additional supplemental material.

The nitrogen source may be any suitable nitrogen source, including but not limited to, ammonium salts, yeast extract, corn steep liquor (CSL), and other protein sources including, but not limited to, denatured proteins recovered from distillation of fermentation broth or extracts derived from the residual separated microbial cell mass recovered after fermentation. Phosphorus may be present in the medium in the form of phosphate salts, such as sodium, potassium, or ammonium phosphates. Sulfur may be present in the medium in the form of sulfate salts, such as sodium or ammonium sulfates. Additional salts include, but are not limited to, magnesium sulfate, manganese sulfate, iron sulfate, magnesium chloride, calcium chloride, manganese chloride, ferric chloride, ferrous chloride, zinc chloride, cupric chloride, cobalt chloride, and sodium molybdate. The growth medium may also contain vitamins such as thiamine hydrochloride, biotin, and para-aminobenzoic acid (PABA). The growth medium may also contain one or more buffering agent(s) (e.g., MES), one or more reducing agent(s) (e.g., cysteine HCl), and/or sodium lactate, which may serve as a carbon source and pH buffer.

Culture Conditions

Optimal culture conditions for various industrially important microorganisms are known in the art.

As required, the culture conditions may be anaerobic, microaerotolerant, or aerobic. Aerobic conditions are those that contain oxygen dissolved in the media such that an aerobic culture would not be able to discern a difference in oxygen transfer with the additional dissolved oxygen, and microaerotolerant conditions are those where some dissolved oxygen is present at a level below that found in air or air saturated solutions and frequently below the detection limit of standard dissolved oxygen probes, e.g., less than 1 ppm. The cultures can be agitated or left undisturbed. Typically, the pH of the media changes over time as the microorganisms grow in number, consume feedstock and excrete organic acids. The pH of the media can be modulated by the addition of buffering compounds to the initial fermentation media in the bioreactor or by the active addition of acid or base to the growing culture to keep the pH in a desired range. Growth of the culture may be monitored by measuring the optical density, typically at a wavelength of 600 nm, or by other methods known in the art.

For converting sugars to ethanol using *S. cerevisiae*, generally, the temperature is about 25° C. to about 35° C. Useful pH ranges for the conversion medium include about 4.0 to about 6.0, about 4.5 to about 6.0, and about 5.5 to about 5.8. The culture is grown under anaerobic conditions without agitation.

*Clostridium* fermentations are generally conducted under anaerobic conditions. For example, ABE fermentations by *C. acetobutylicum* are typically conducted under anaerobic conditions at a temperature in the range of about 25° C. to about 40° C. Historically, suspension cultures did not use agitators, but relied on evolved or sparged gas to mix the contents of the bioreactors. Cultures, however, can be agitated to ensure more uniform mixing of the contents of the bioreactor. For immobilized cultures, a bioreactor may be run without agitation in a fixed bed (plug flow) or fluidized/expanded bed (well-mixed) mode. Thermophilic bacterial fermentations can reach temperatures in the range of about 50° C. to about 80° C. In some embodiments, the temperature range is about 55° to about 70° C. In some embodiments, the temperature range is about 60° C. to about 65° C. For example, Clostridium species such as *C. thermocellum* or *C. thermohydrosulfuricum* may be grown at about 60° C. to about 65° C. The pH of the *Clostridium* growth medium can be modulated by the addition of buffering compounds to the initial fermentation media in the bioreactor or by the active addition of acid or base to the growing culture to keep the pH in a desired range. For example, a pH in the range of about 3.5 to about 7.5, or about 5 to about 7, may be maintained in the medium for growth of *Clostridium*.

Immobilization of Microorganisms on Solid Support

Immobilization of the microorganism, from spores or vegetative cells, can be by any known method.

In one embodiment, entrapment or inclusion in the support is achieved by polymerizing or solidifying a spore or vegetative cell containing solution. Useful polymerizable or solidifiable solutions include, but are not limited to, alginate, κ-carrageenan, chitosan, polyacrylamide, polyacrylamide-hydrazide, agarose, polypropylene, polyethylene glycol, dimethyl acrylate, polystyrene divinyl benzene, polyvinyl benzene, polyvinyl alcohol, epoxy carrier, cellulose, cellulose acetate, photocrosslinkable resin, prepolymers, urethane, and gelatin.

In another embodiment, the microorganisms are incubated in growth medium with a support. Useful supports include, but are not limited to, bone char, cork, clay, resin, sand, porous alumina beads, porous brick, porous silica, celite (diatomaceous earth), polypropylene, polyester fiber, ceramic, (e.g., porous ceramic, such as porous silica/alumina composite), lava rock, vermiculite, ion exchange resin, coke, natural porous stone, macroporous sintered glass, steel, zeolite, engineered thermal plastic, concrete, glass beads, Teflon, polyetheretherketone, polyethylene, wood chips, sawdust, cellulose fiber (pulp), or other natural, engineered, or manufactured products. The microorganisms may adhere to the support and form an aggregate, e.g., a biofilm.

In another embodiment, the microorganism is covalently coupled to a support using chemical agents like glutaraldehyde, o-dianisidine (U.S. Pat. No. 3,983,000), polymeric isocyanates (U.S. Pat. No. 4,071,409), silanes (U.S. Pat. Nos. 3,519,538 and 3,652,761), hydroxyethyl acrylate, transition metal-activated supports, cyanuric chloride, sodium periodate, toluene, or the like. See also U.S. Pat. Nos. 3,930,951 and 3,933,589.

In one embodiment, immobilized spores, such as those of *Clostridium*, e.g., *C. acetobutylicum*, are activated by thermal shock and then incubated under appropriate conditions in a growth medium whereby vegetative growth ensues. These cells remain enclosed in or on the solid support. After the microorganisms reach a suitable density and physiological state, culture conditions can be changed for bioproduct, e.g., solvent, production. If the immobilized cells lose or exhibit reduced bioproduct, e.g., solvent, production ability, they can be reactivated by first allowing the cells to sporulate before repeating the thermal shock and culture sequence.

Vegetative cells can be immobilized in different phases of their growth. For microorganisms that display a biphasic culture, such as *C. acetobutylicum* with its acidogenic and solventogenic phases, cells can be immobilized after they enter the desired culture phase in order to maximize production of the desired products, where in the case of *C. acetobutylicum* it is the organic acids acetic acid and butyric acid in the acidogenic phase and the solvents acetone, butanol and ethanol in the solventogenic phase. Alternatively, biphasic cells can be immobilized in the acidogenic phase and then adapted for solvent production.

In some embodiments, microorganisms to be immobilized in a bioreactor are introduced by way of a cell suspension. Generally, these microorganisms are dispersed in the media as single cells or small aggregates of cells. In other embodiments, the microorganisms are introduced into the bioreactor through the use of suspended particles that are colonized by the microorganisms. These suspended particles can be absorbed onto the solid support and frequently are of sufficiently small size that they can enter and become immobilized in the pore structures of the solid support. Typically, regardless of the suspended particle size, microorganisms can be transferred by contact with the solid support. A biofilm on the introduced particles can transfer to and colonize these new surfaces. In some embodiments, the desired characteristics of the microorganisms can only be maintained by culturing on a solid support, thereby necessitating the use of small colonized particle suspensions for seeding a solid support in a bioreactor.

Support for Immobilized Microbial Growth

In some embodiments, a bioproduct-producing, e.g., solvent-producing, microorganism is grown in an immobilized form on a solid or semi-solid support material in a bioreactor as described herein. In some embodiments, the support comprises a porous material. Non-limiting examples of suitable support materials include bone char, synthetic polymers, natural polymers, inorganic materials, and organic materials.

Natural polymers include organic materials such as cellulose, lignocellulose, hemicellulose, and starch. Organic materials include feedstock such as plant residue and paper. Composites of two or more materials may also be used such as mixtures of synthetic polymer with natural plant polymer.

Examples of semi-solid media include alginate, κ-carrageenan and chitosan, polyacrylamide, polyacrylamide-hydrazide, agarose, polypropylene, polyethylene glycol, dimethyl acrylate, polystyrene divinyl benzene, polyvinyl benzene, polyvinyl alcohol, epoxy carrier, cellulose, cellulose acetate, photocrosslinkable resin, prepolymers, urethane, and gelatin. Examples of solid support include cork, clay, resin, sand, porous alumina beads, porous brick, porous silica, celite, wood chips or activated charcoal.

Suitable inorganic solid support materials include inorganic materials with available surface hydroxy or oxide groups. Such materials can be classified in terms of chemical composition as siliceous or nonsiliceous metal oxides. Siliceous supports include, inter alia, glass, colloidal silica, wollastonite, cordierite, dried silica gel, bentonite, and the like. Representative nonsiliceous metal oxides include alumina, hydroxy apatite, and nickel oxide.

In some embodiments, the support material is selected from bone char, polypropylene, steel, diataomaceous earth, zeolite, ceramic, (e.g., porous ceramic, such as porous silica/alumina composite), engineered thermal plastic, clay brick, concrete, lava rock, wood chips, polyester fiber, glass beads, Teflon, polyetheretherketone, polyethylene, vermiculite, ion exchange resin, cork, resin, sand, porous alumina beads, coke, natural porous stone, macroporous sintered glass, or a combination thereof. In one embodiment, the support material is bone char. Useful support material has a high surface area to volume ratio such that a large amount of active, productive cells can accumulate in the bioreactor. Useful supports may contain one or more macrostructured components containing one or more useful support material(s) that promotes good fluidmechanical properties, for example, a wire mesh/gauze packing material used for traditional distillation tower packing.

In some embodiments, the support material includes a surface area of at least about 100 $m^2/m^3$. In some embodiments, the support material comprises a bulk density of at least about 0.15 $g/cm^3$. In some embodiments, the support material comprises a ball-pan hardness number of at least about 60. In some embodiments, the support material comprises a yield strength of at least about 20 MPa.

The particle size for the support material will vary depending upon bioreactor configuration and operation parameters. In some embodiments, the support material is sized by sieving. In some embodiments, the particles are classified by the sieve number of the mesh that they can pass through. In some embodiments, the particles are sieved with a mesh that has a U.S. Sieve Number of 3½, 4, 5, 6, 7, 8, 10, 12, 14, 16, 18, 20, 25, 30, 35, 40, 45, 50, 60, or 70. In some embodiments, the particles are sieved at least twice, first using a mesh with larger openings followed by a mesh with smaller openings to yield particles within a defined particle size distribution range. In some embodiments, the particles are at least about 100 µm, 200 µm, 300 µm, 400 µm, 500 µm, 600 µm, 700 µm, 800 µm, 900 µm, 1000 µm, 1,100 µm, 1,200 µm, 1,300 µm, 1,400 µm, 1,500 µm, 1,600 µm, 1,700 µm, 1,800 µm, 1,900 µm, 2,000 µm, 3,000 µm, 4,000 µm, 5,000 µm, 6,000 µm, 7,000 µm, 8000 µm, 9,000 µm, 10,000 µm, 12,500 µm, 15,000 µm, 17,500 µm, 20,000 µm, 22,500 µm, or 25,000 µm in diameter. In some embodiments, the particles are less than about 100 µm, 200 µm, 300 µm, 400 µm, 500 µm, 600 µm, 700 µm, 800 µm, 900 µm, 1000 µm, 1,100 µm, 1,200 µm, 1,300 µm, 1,400 µm, 1,500 µm, 1,600 µm, 1,700 µm, 1,800 µm, 1,900 µm, 2,000 µm in diameter. In further embodiments, at least about 80%, 85%, 90%, 95%, or 100% of the particle have diameters that are in the range of about 100-400 µm, 100-600 µm, 100-800 µm, 200-500 µm, 200-800 µm, 200-1000 µm, 400-800 µm, 400-1000 µm, 500-1000 µm, 600-1,200 µm, 800-1,400 µm, 1,000-1,500 µm, 1,000-2000 µm, 2,000-4,000 µm, 4,000-6,000 µm, 5,000-12,000 µm, 3,000-15,000 µm, or 6,000-25,000 µm. In some embodiments, the particle diameters are the equivalent diameters, a parameter that takes into account the irregular shapes of the individual particles.

Ideally, the semi-solid or solid support material should have a high surface area. This can be achieved through the use of small sized particles, particles with high porosity, or a combination thereof. In some embodiments, the surface area of the particles is at least about 0.003 $m^2/g$, 0.01 $m^2/g$, 0.02 $m^2/g$, 0.05 $m^2/g$, 0.1 $m^2/g$, 0.5 $m^2/g$, 1 $m^2/g$, 5 $m^2/g$, 10 $m^2/g$, 25 $m^2/g$, 50 $m^2/g$, 75 $m^2/g$, 100 $m^2/g$, 125 $m^2/g$, 150 $m^2/g$, 175 $m^2/g$, 200 $m^2/g$, 225 $m^2/g$, 250 $m^2/g$, 275 $m^2/g$, 300 $m^2/g$, 325 $m^2/g$, 350 $m^2/g$, 375 $m^2/g$, 400 $m^2/g$, 425 $m^2/g$, 450 $m^2/g$, 500 $m^2/g$, 600 $m^2/g$, 700 $m^2/g$, 800 $m^2/g$, 900 $m^2/g$, 1000 $m^2/g$, or 2000 $m^2/g$. Additionally, the bulk density should be sufficiently high so that the smallest particles settle out of the fluid stream in the column expansion zone and/or particle disengagement zone and are thereby retained in the bioreactor. In some embodiments, the bulk density of the support is at least about 0.1 $g/cm^3$, 0.2 $g/cm^3$, 0.3 $g/cm^3$, 0.4 $g/cm^3$, 0.5 $g/cm^3$, 0.6 $g/cm^3$, 0.7 $g/cm^3$, 0.8 $g/cm^3$, 0.9 $g/cm^3$, 1.0 $g/cm^3$, 1.1 $g/cm^3$, 1.2 $g/cm^3$, or 1.3 $g/cm^3$. The support material should have sufficient hardness to resist abrasion and thereby avoid appreciable dust formation when the support particles touch or collide with each other. In some embodiments, the support has a ball-pan hardness number of at least about 20, 40, 60, 80, 100, 120, 140, 160 or 200. The support material should also have sufficient tensile strength to resist shattering due to internal stresses, which may be caused by the growth of biofilms inside support material pores. In some embodiments, the support has a yield strength of at least about 20 MPa, 40 MPa, 60 MPa, 80 MPa, 100 MPa, 120 MPa, 140 MPa, 160 MPa, 180 MPa, 200 MPa, 300 MPa, or 400 MPa. The support material should also have the ability to resist being crushed by the accumulated weight of material above it. Crush strength is another measurement of the mechanical strength of the support and is typically a function of the composition, shape, size, and porosity of the material (increase in port volume may negatively impact particle strength). In some embodiments, the crush strength is at least about 8 kg.

In some embodiments, the support material is chosen to support growth of the fermenting bioproduct-producing, e.g., solvent-producing microorganism as a biofilm. The biofilm may grow on exterior surfaces of support particles, in the fluid space between support particles, and/or on surfaces in the interior of pores of the support material.

Recovery Processes

The fermentation effluent containing the bioproduct, e.g., solvent, product may be concentrated and/or purified. In some embodiments, the product is concentrated prior to further purification using any suitable concentration technique known in the art, including but not limited to mechanical vapor recompression (MVR) distillation, pervaporation, and liquid-liquid extraction.

In some embodiments, fermentation product streams from multiple bioreactors or series of bioreactors are combined prior to further purification. In some embodiments, fermentation product streams from multiple bioreactors or series of bioreactors are fed to separate purification units. For example, a fermentation product stream from a first bioreactor processing C5 sugars can be combined with fermentation products from a second bioreactor processing C5 and C6 sugars. Alternatively, the product streams from the first and second bioreactors may be processed separately.

In other configurations, fermentation broth may be separated from products in situ (i.e., extractive fermentation) by any of a variety of methods (e.g., LLE (liquid-liquid extraction), vacuum distillation, stripping, pervaporation), to increase the total productivity of the overall conversion process. For example, a solvent may be recovered from the bioreactor by condensation of the sparging and naturally occurring gases.

In some embodiments, MVR distillation is used for concentration of solvent from the microbial fermentation medium. In this approach, overhead vapors generated as part of the distillation process are mechanically compressed, and the resulting latent heat released from the condensation process is supplied to the evaporation process. In some embodiments, MVR reduces separation energy requirements by at least about 80% in comparison to conventional distillation.

In some embodiments, a conventional distillation process is used for the remaining product separation, optionally with thermally cascaded heat integration. Distillation avoids the impact of secondary compounds on the separation process since surface chemistry is not the basis for the separation.

Continuous Process

In some embodiments, a continuous process for bioproduct, e.g., solvent, production is provided. In a continuous production process herein, a carbohydrate-containing feedstock containing soluble sugar molecules is continuously fed to one or more bioreactors for microbial production of the bioproduct, e.g., solvent, the bioproduct is continuously produced by immobilized microorganism(s) in the one or more bioreactors, and bioproduct-containing effluent, i.e., fermentation broth, is continuously withdrawn from the one or more reactors, for the duration of fermentation. In some embodiments, feedstock is continuously pretreated to produce soluble sugar molecules, for example, continuously hydrolyzed to release soluble sugar molecules. In one embodiment, the feedstock is lignocellulosic feedstock, and is hydrolyzed with nitric acid to release soluble sugar molecules from cellulose and hemicellulose, as described supra.

In some embodiments, the continuous process may also include downstream continuous concentration and/or purification processes for recovery of the bioproduct, e.g., solvent product, wherein continuously withdrawn effluent is continuously processed in one or more concentration and/or purification processes to produce a bioproduct, e.g., solvent product.

In some embodiments, the process may also include a conditioning process to remove inhibitors of microbial growth and/or bioproduct, e.g., solvent production, as described herein. The conditioning process may operate continuously downstream from a feedstock hydrolysis process, and upstream from the bioreactor(s), and conditioned hydrolyzed feedstock may be continuously fed to the bioreactor for the duration of fermentation.

In some embodiments, the process may also include deconstruction of the feedstock and/or removal of extractives from the feedstock, as described herein. Deconstruction and/or removal of extractives may be continuous or may occur prior to or periodically throughout the continuous process.

In some embodiments, the process operates continuously for at least about 50, 100, 200, 300, 400, 600, 800, 1000, 1350, 1600, 2000, 2500, 3000, 4000, 5000, 6000, 7000, 8000, or 8400 hours.

A "continuous" process as described herein may include periodic or intermittent partial or complete shutdowns of one or more parts of the bioproduct, e.g., solvent, production system for processes such as maintenance, repair, regeneration of resin, etc.

Continuous fermentation, with constant feed of feedstock and withdrawal of product-containing microbial broth, can minimize the unproductive portions of a fermentation cycle, such as lag, growth, and turnaround time, thereby reducing the capital cost, and can reduce the number of inoculation events, thus minimizing operational costs and risk associated with human and process error.

The continuous methods and systems described herein can utilize one or more, e.g., one, two, or three or more, bioreactors. When multiple (two or more) bioreactors are used, they may be arranged in parallel, series, or a combination thereof. The bioreactors can grow the same or different strains of microorganism(s). The strains can be different based on the type of sugar they metabolize to maximize bioproduct, e.g., solvent production. For example, a first bioreactor or multiple bioreactors arranged in parallel, series, or a combination thereof can grow a strain that has been selected to metabolize C5 sugars and a second bioreactor or multiple bioreactors arranged in parallel, series, or a combination thereof can grow another strain that has been selected to metabolize C5 and C6 sugars. The bioreactors may be coupled to an upstream feedstock hydrolysis unit, and may also be coupled to a downstream recovery/separation unit. A first bioreactor or multiple bioreactors arranged in parallel, series, or a combination thereof with a strain that metabolizes C5 sugars can be coupled to an upstream first stage hydrolysis module of a nitric acid hydrolysis unit for hydrolysis of lignocellulosic feedstock. A second bioreactor or multiple bioreactors arranged in parallel, series, or a combination thereof with a strain that metabolizes C5 and C6 sugars can be coupled to an upstream second stage hydrolysis module of a nitric acid hydrolysis unit for hydrolysis of a lignocellulosic feedstock. Alternatively, the same bioreactor or multiple bioreactors arranged in parallel, series, or a combination thereof may be used for conversion of both C5 and C6 sugars to bioproduct, e.g., solvent. For example, both first and second stage nitric acid hydrolysates of a lignocellulosic feedstock may be added either separately or as a combined mixture to the bioreactor(s).

In some embodiments of continuous bioproduct, e.g., solvent, production processes and systems described herein, butanol may be produced by a microbial strain, such as a *Clostridium* strain, at a titer of about or at least about 5, 6, 7, 8, 10, 12, 15, 20, 25, 30, 40, 50, 60, 70, 80, or 90 g butanol per liter, or about 5 to about 90, about 5 to about 10, about 8 to about 20, about 15 to about 30, about 25 to about 50, about 40 to about 80, or about 60 to about 90 g butanol per liter. In some embodiments of continuous bioproduct, e.g., solvent, production processes and systems described herein, butanol may be produced by a microbial strain, such as a *Clostridium* strain, with a yield of about or at least about 30, 35, 40, 50, or 60% or about 30% to about 60%, about 40% to about 60%, or about 50% to about 60%. In some embodiments of continuous bioproduct, e.g., solvent, production processes and systems described herein, butanol may be produced by a microbial strain, such as a *Clostridium* strain, with a productivity of about or at least about 1, 3, 5, 10, 15, or 20 g, butanol per liter per hour, or about 1 to about 20, about 3 to about 10, about 5 to about 15, or about 10 to about 20 g butanol per liter per hour. In some embodiments, butanol titer is greater than about 90 g/L, and water saturated butanol may be skimmed off the top of the liquid in the bioreactor.

The following examples are intended to illustrate, but not limit, the invention.

EXAMPLES

Example 1

Salt Selection of Butanol-Tolerant Mutants of Co-9064

The Minimum Inhibitory Concentration (MIC) for NaCl was determined for butanol-producing *Clostridium* species strain Co-9064, an oxygen tolerant mutant of Co-6636, an environmental isolate, to determine the highest concentration of salt at which this strain would grow. Once this was determined, 30 selection plates were prepared at the highest concentration at which growth was observed (300 mM) plus 25 mM (325 mM). The plates contained the added salt, growth medium suitable for fermentation of Co-9064, and agar. The plates were placed in an anaerobic hood 24 hours in advance of their use to allow enough time for the plates to become anaerobic.

A seed train of Co-9064 was prepared the night before use to provide 50 ml of log phase culture for mutagenesis in the morning. Cells were mutagenized with 40 µg/ml N-methyl-N'-nitro-N-nitrosoguanidine (MNNG) and then recovered for 4 hours in media that was supplemented with 100 mM NaCl.

100 µA of recovered cells were plated on each selection plate. The plates were incubated anaerobically for 48-72 hours at 32° C. Colonies that grew on selection plates were then restreaked on fresh selection plates containing 325 mM NaCl for 48-72 hours at 32° C., to obtain single colonies.

Figure 3:
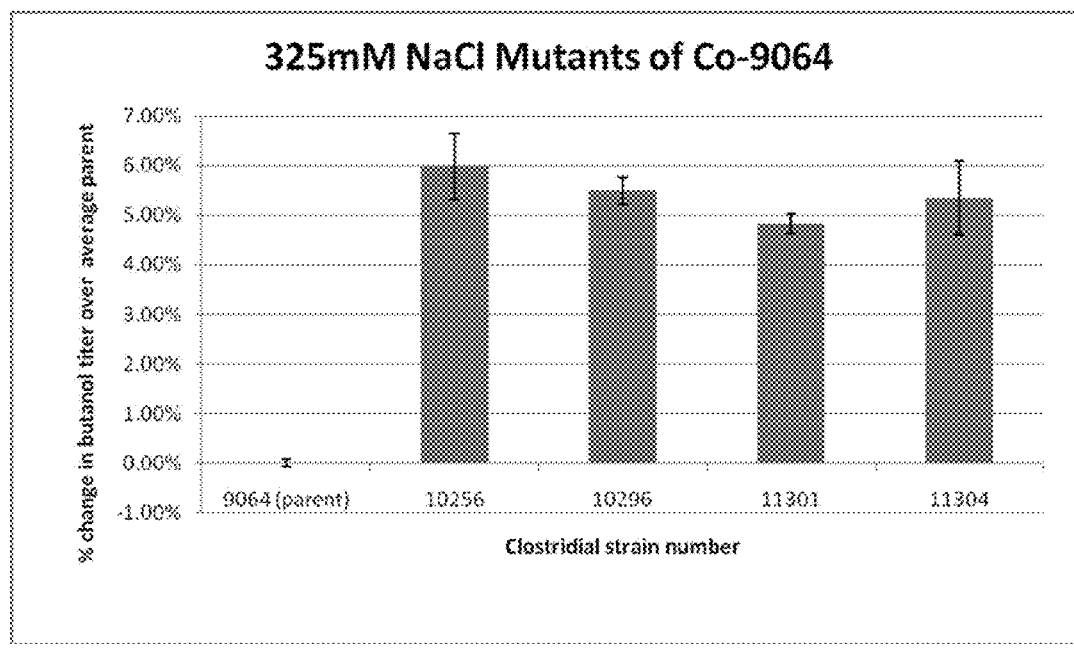
FIG. 3 shows butanol titers, of individual mutants selected in the salt selection method described in Example 1 in comparison with the butanol titer of the parent strain. All of the selected mutants exhibited higher butanol titers than the parent strain Co-9064.

A representative colony from each restreak was incubated in 2.5 ml liquid medium without added salt for 72 hours at 32° C. Cultures were then harvested and prepped for HPLC to determine butanol titer. Colonies with the highest titers were fermented again in triplicate. The colonies with the highest titers of these triplicates were then spore stocked and tested again at a larger scale in duplicate, 60 ml. The results from the larger scale test are shown in FIG. 3.

Figure 2:
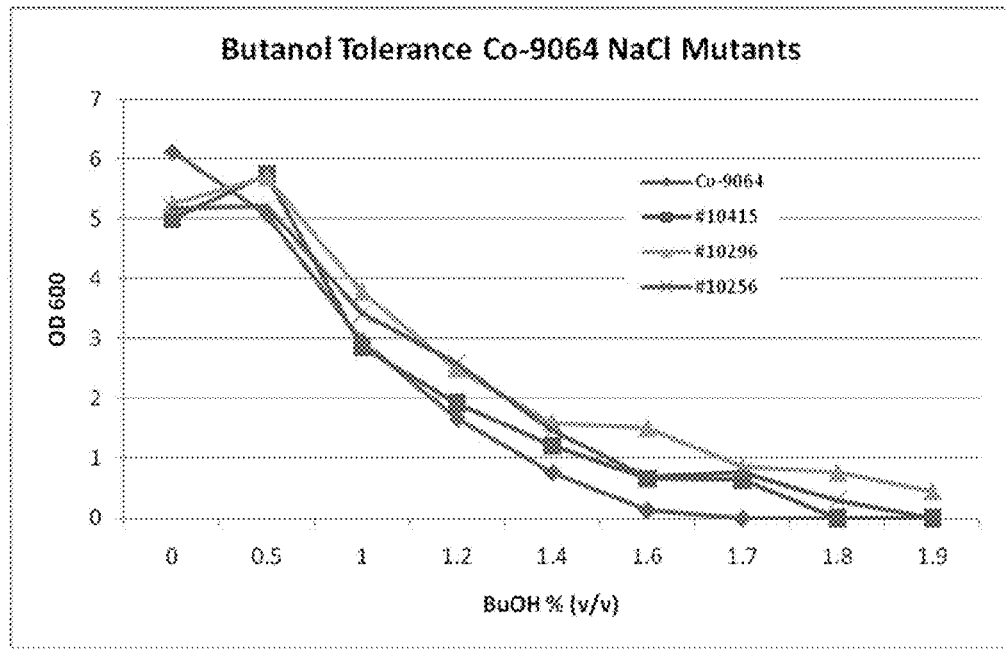
FIG. 2 shows butanol tolerance of mutants selected as described in Example 1.
Figure 2:
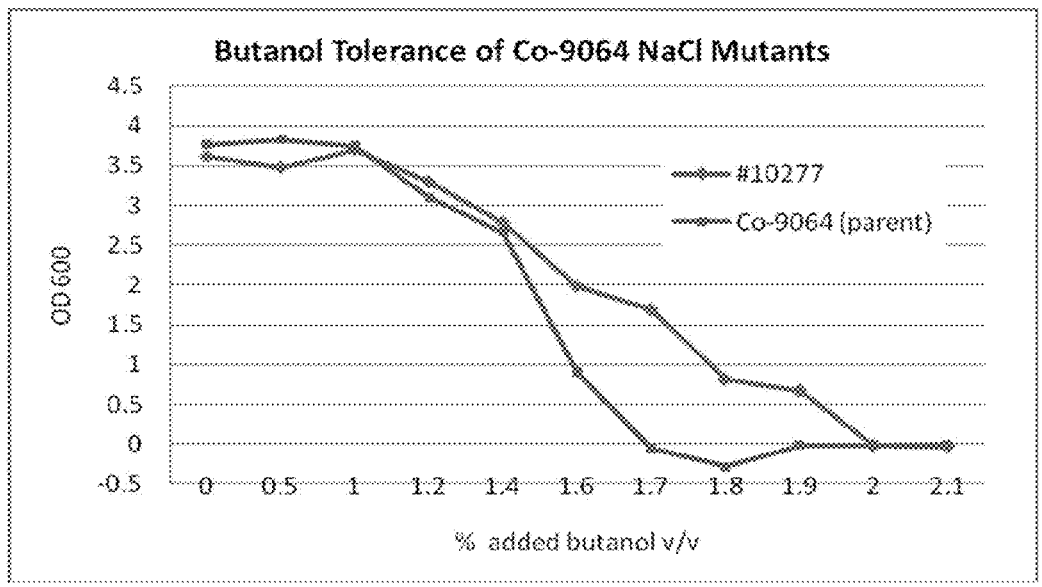

Compared to the parent strain, the strains selected in the salt screen exhibited a shift to the right when graphed at normal distribution. (FIG. 1). These strains also exhibited improved butanol tolerance when grown at increasing concentrations of butanol. (FIGS. 2A and 2B) Further, when salt MIC was assessed, salt tolerance in the mutants increased by more than 100 mM when compared to the parent strain. Mutants 11303, 11301, 10277, and 10256 grew on plates containing up to 450 mM NaCl, in comparison with the parent strain, which only grew on plates containing up to 325 mM NaCl.

Example 2

Salt Selection of Mutants of Co-1533 with Increased Butanol Titer

The MIC for NaCl was determined for butanol-producing *Clostridium* species strain Co-1533, a butanol tolerant mutant of Co-1719, an environmental isolate, to determine the highest concentration of salt at which this strain would grow. Once this was determined, 30 selection plates were prepared at the highest concentration at which growth was observed (275 mM) plus 25 mM (300 mM). The plates contained the added salt, growth medium suitable for fermentation of Co-1533, and agar. The plates were placed in an anaerobic hood 24 hours in advance of their use to allow enough time for the plates to become anaerobic.

A seed train of Co-1533 was prepared the night before use to provide 50 ml of log phase culture for mutagenesis in the morning. Cells were mutagenized with 30 µg/ml EMS and then recovered for 4 hours in media that was supplemented with 100 mM NaCl.

100 µl of recovered cells were plated on each selection plate. The plates were incubated anaerobically for 48-72 hours at 30° C. Colonies that grew on selection plates were restreaked on fresh selection plates containing 300 mM NaCl for 48-72 hours at 30° C., to obtain single colonies.

Figure 4:
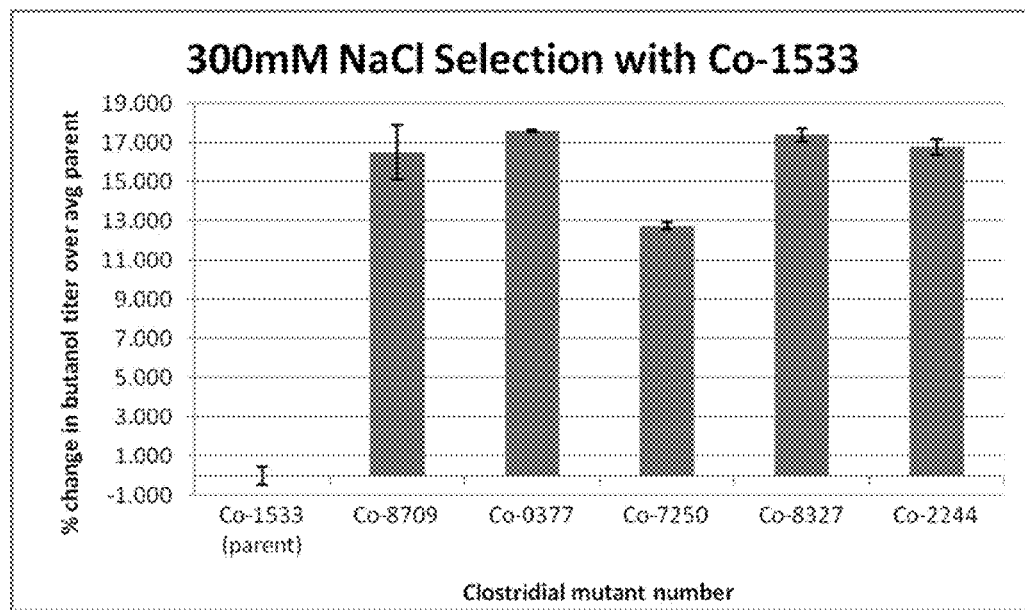
FIG. 4 shows the results of a selection for mutants with increased butanol titer, as described in Example 2
Figure 4:
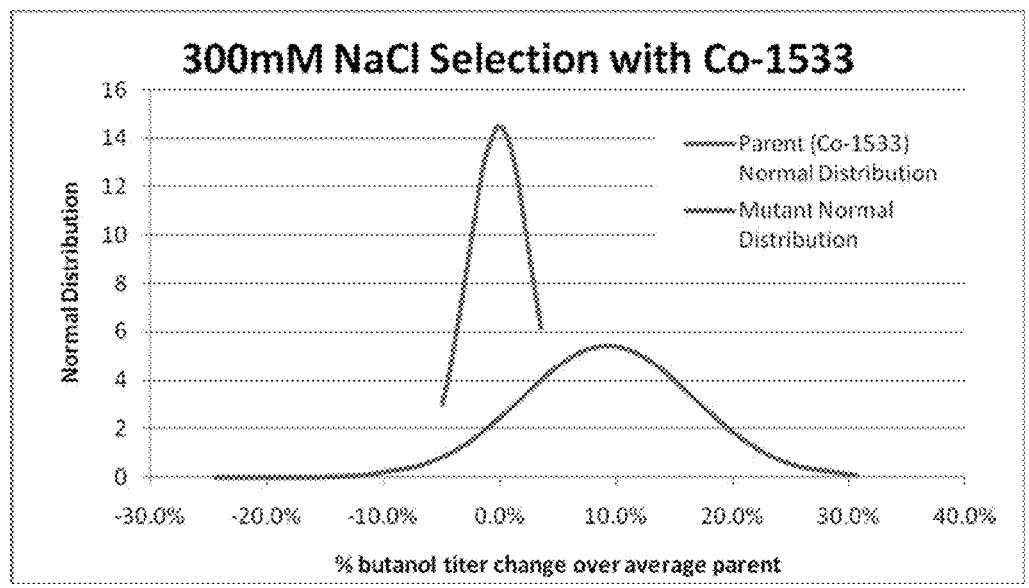

A representative colony from each restreak was incubated in 2.5 ml liquid medium without added salt for 72 hours at 30° C. Cultures were then harvested and prepped for HPLC to determine butanol titer. Colonies with the highest titers were fermented again in triplicate. The colonies with the highest titers of these triplicates were then glycerol stocked and tested again at a larger scale in duplicate, 60 ml. The results from the larger scale test are shown in FIG. 4A. All five mutants included in FIG. 4A exhibited a significant increase in butanol titer ranging from 13-18% higher than the parent (Co-1533).

Compared to the parent strain, the strains selected in the salt screen exhibited a shift to the right when graphed at normal distribution. (FIG. 4B).

Example 3

Salt Selection of Mutants of Co-6232 with Increased Butanol Titer. A Second Round of Salt Selection to Select Mutants with Further Improvement in Butanol Titer The MIC for NaCl was determined for butanol-producing *Clostridium* species strain Co-6232, a mutant of a salt mutant Co-4624, a $4^{th}$ generation mutant of an environmental isolate. Once this was determined, 30 selection plates were prepared at the highest concentration of salt at which growth was observed (325 mM) plus 25 mM (350 mM). The plates contained the added salt, growth medium suitable for fermentation of Co-6232, and agar. The plates were placed in an anaerobic hood 24 hours in advance of their use to allow enough time for the plates to become anaerobic.

A seed train of Co-6232 was prepared the night before use to provide 50 ml of log phase culture for mutagenesis in the morning. Cells were mutagenized with 43.2 μg/ml EMS and then recovered for 4 hours in media that was supplemented with 100 mM NaCl.

100 μl of recovered cells were plated on each selection plate. The plates were incubated anaerobically for 48-72 hours at 30° C. Colonies that grew on selection plates were then restreaked on fresh selection plates containing 350 mM NaCl for 48-72 hours at 30° C., to obtain single colonies.

Figure 5:
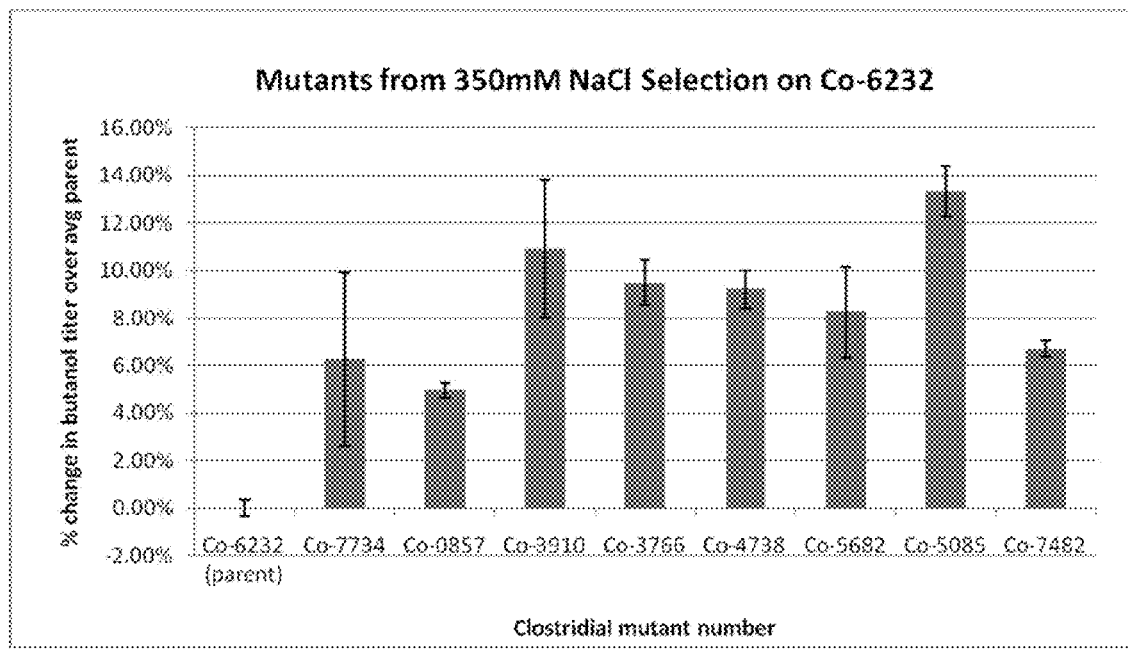
FIG. 5 shows the results of a second round of selection for mutants with increased butanol titer, as described in Example 3.
Figure 5:
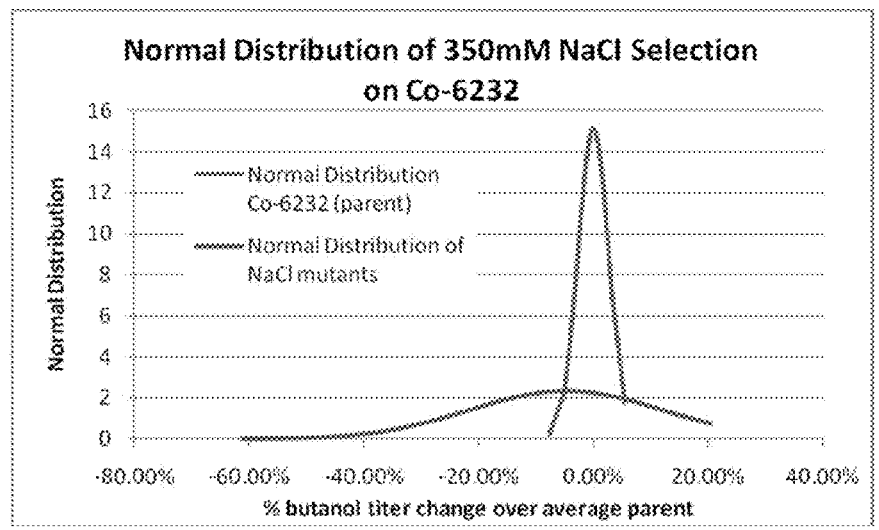

A representative colony from each restreak was incubated in 2.5 ml liquid medium without added salt for 72 hours at 30° C. Cultures were then harvested and prepped for HPLC to determine butanol titer. Colonies with the highest titers were fermented again in triplicate. The colonies with the highest titers of these triplicates were then glycerol stocked and tested again at a larger scale in duplicate, 60 ml. The results from the larger scale test area shown in FIG. 5A. All eight mutants included in FIG. 5A exhibited a significant increase in butanol titer ranging from 5-13% higher than the parent (Co-6232). Compared to the parent strain, the strains selected in the salt screen exhibited a shift to the right when graphed at normal distribution. (FIG. 5B).

Example 4

Increased Resistance to Mutagenesis by Salt Selection Mutants

Co-2164, a third generation NaCl salt mutant of Co-5673, and Co-5673, an environmental isolate, were both grown to log phase in liquid medium. Each strain was spun down separately and resuspended in 1.5 ml of 0.1M citrate buffer, pH 5.5. For each strain, three 500 μl aliquots were then transferred into three separate 1.7 ml microcentrifuge tubes. One tube contained 50 μg/ml MNNG, one tube contained 30 μg/ml EMS, and a third tube contained no mutagen as a control. Cells were incubated at 32° C. for 40 minutes and then washed twice with medium. The cells were suspended in liquid medium for 4 hours and then plated at different dilutions to determine survival. Co-2164 exhibited an 80% higher survival rate in MNNG and a 10% higher survival rate in EMS, in comparison to Co-5673. The data are summarized below in Table 2.

TABLE 2

Survival of Salt Mutant and Parent Strains in Mutagens

| Strain | EMS | MNNG | Control |
|---|---|---|---|
| Co-5673 | $3.8 \times 10^6$ (4%) | $3.7 \times 10^6$ (4%) | $9.8 \times 10^7$ |
| Co-2164 | $5.8 \times 10^6$ (14%) | $3.5 \times 10^7$ (84%) | $4.16 \times 10^7$ |

Example 5

Altered Morphology in Salt Selection Mutants

Morphological differences were observed when a second round of NaCl selection was performed.

The parent strain, Co-2614, is a 325 mM NaCl mutant of Co-9064. Co-9064, is a third generation mutant of Co-5673, a *Clostridium* environmental isolate. The mutant, #14068 is a 450 mM NaCl mutant of Co-2614. 60 ml cultures were inoculated at 1:20 from a log phase culture.

Figure 6A:
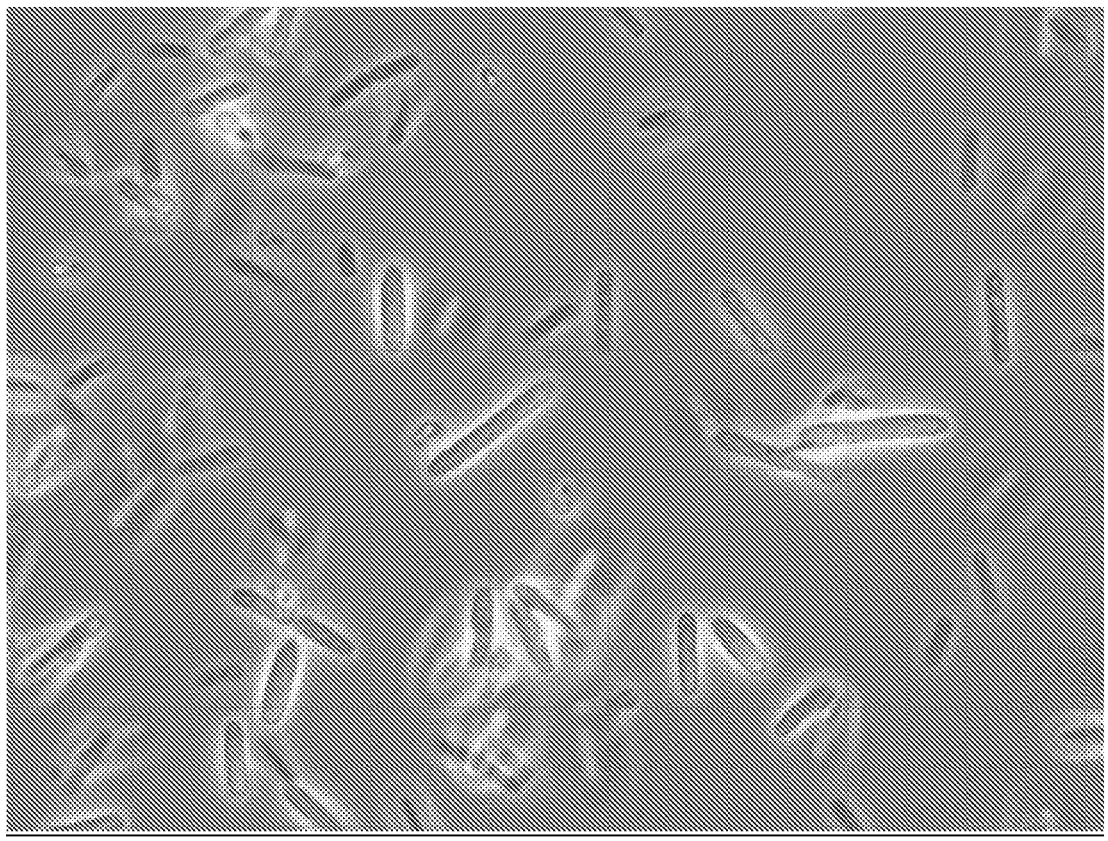
FIG. 6A shows the parent, Co-2614, 40 hours after inoculation.
Figure 6B:
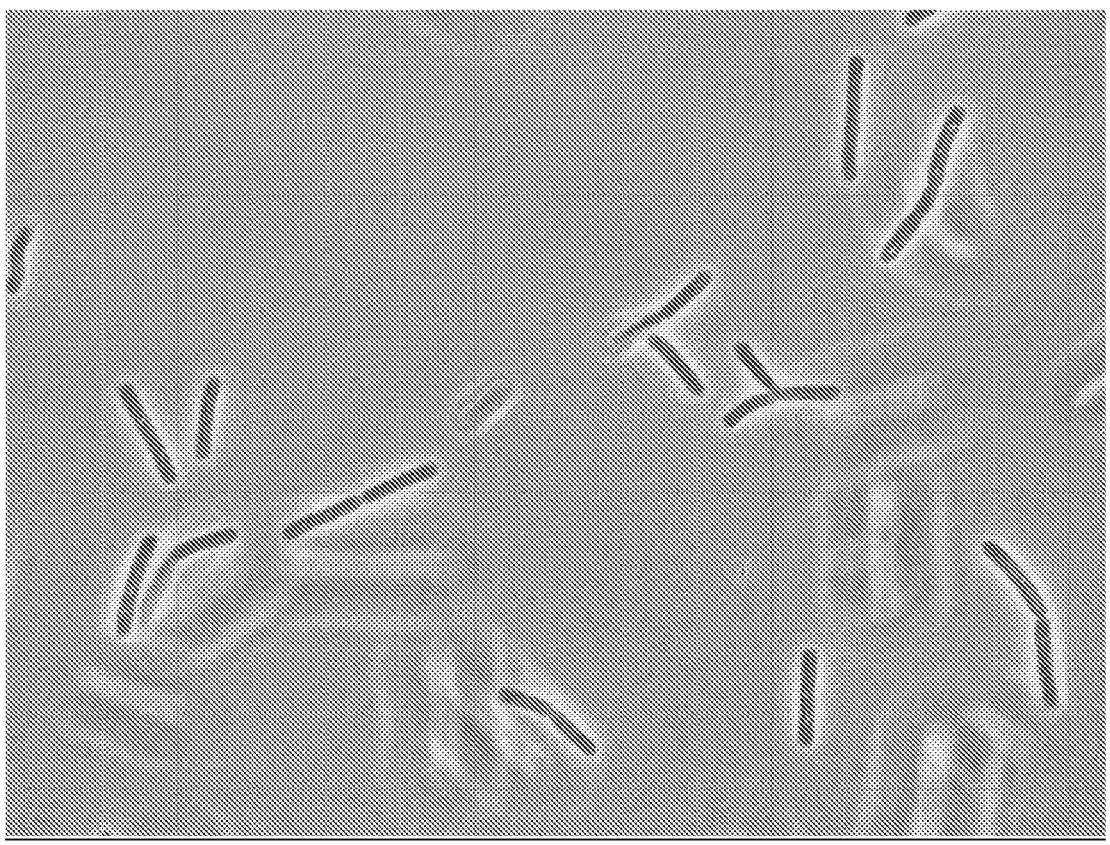
FIG. 6B shows the mutant, 14068, 92 hours after inoculation. At 92 hours, a segmented Clostridial form persists.
Figure 6C:
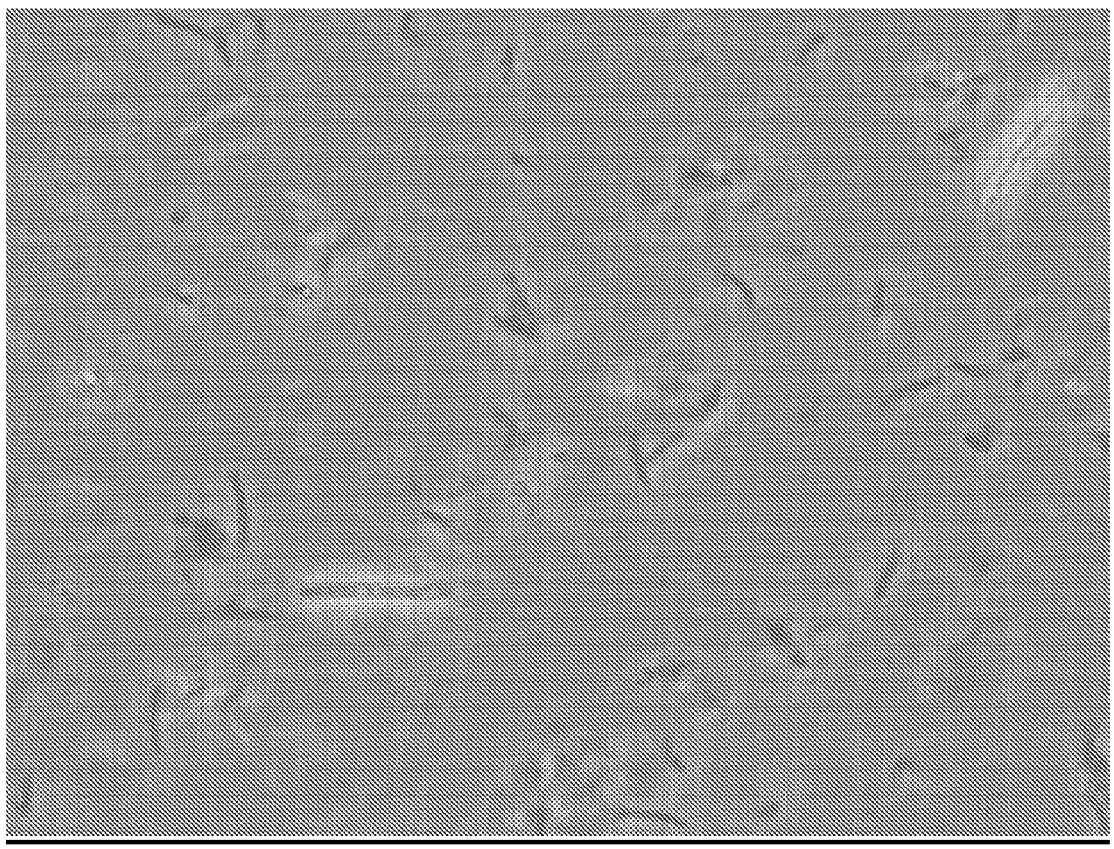
FIG. 6C shows the mutant, 14098, 92 hours after inoculation. The parent, Co-2614, had no living cells at 92 hours.

Microscopy images were taken of these cultures at 40 hrs and 92 hrs using a 100× objective. FIG. 6A shows the parent, Co-2614, at 40 hrs post-inoculation. Note that the majority of cells were in a Clostridial (solventogenic) form. FIG. 6B shows the mutant, #14068 at 40 hrs post-inoculation. Note that the majority of cells were thin and as so, still appeared to be in a vegetative (exponential-growth) phase of their life cycle. The cells appeared to have just started to become granular (as seen in Clostridial forms), but lacked the cigar-shaped, larger formation of the parent. At 92 hrs, Co-2614's culture contained only cell debris (not pictured). In contrast, as shown in FIG. 6C, #14068 had a segmented, granular-type Clostridial form which still persisted in the culture.

Example 6

Salt Selection Mutants with Increased Osmotic Tolerance

A parent *Clostridium* strain and four mutants, selected for growth on salt selection medium as described in Example 1, were grown on agar plates with varying amounts of NaCl in the growth medium. The plates were prepared with NaCl concentrations ranging from 350 mM to 475 mM, placed in an anaerobic hood overnight, and then spread with 100 μl undiluted log phase cultures. The plates were checked after 48 hours for growth, and colony forming units (CFUs) were assessed for each plate. The results are shown in Table 3.

TABLE 3

Osmotic Tolerance of Salt Mutants and Parent Strain

| NaCl Concentration | CFU/ml | | | | |
|---|---|---|---|---|---|
| (mM) | 11303 | 11301 | 10277 | 10256 | Parent |
| 350 | lawn | lawn | lawn | lawn | 6000 |
| 400 | lawn | lawn | lawn | lawn | 0 |
| 425 | 800 | 220 | 2930 | 480 | 0 |
| 450 | 10 | 30 | 150 | 20 | 0 |
| 475 | 0 | 0 | 0 | 0 | 0 |

"Lawn" refers to bacterial growth that was spread all over the surface of the plate. No single colonies were observed, and no inhibition of growth was observed at these levels of salt.

The parent is much less tolerant to NaCl in the solid medium than the mutants. The parent exhibited no growth at 400 mM NaCl and higher, whereas four of the mutants all exhibited growth up to 450 mM salt.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims.

All publications, patents, and patent applications cited herein are hereby incorporated by reference in their entireties for all purposes and to the same extent as if each individual publication, patent, or patent application were specifically and individually indicated to be so incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

I claim:

1. A method for selecting a microbial strain with increased tolerance to a bioproduct that is produced by and is toxic to said microbial strain, comprising culturing mutants of a bioproduct-producing microbial strain on solid growth medium or in liquid growth medium that comprises salt at a concentration sufficient to inhibit growth of the bioproduct-producing microbial strain by at least about 99%, selecting microbial colonies that grow in the presence of said salt, and identifying a bioproduct tolerant microbial strain by assessing the bioproduct tolerance of said colonies.

2. A method according to claim 1, wherein bioproduct tolerance is at least about 5% higher in the bioproduct tolerant microbial strain relative to the bioproduct-producing microbial strain from which it was derived.

3. A method according to claim 1, wherein the bioproduct is a solvent.

4. A method according to claim 3, wherein the solvent comprises butanol.

5. A method according to claim 1, wherein the growth medium comprises at least about 50 mM salt.

6. A method according to claim 1, wherein the microbial strain is bacterial or fungal.

7. A method according to claim 6, wherein the microbial strain is a bacterial species of *Clostridium, Lactobacillus, Enterococcus, Escherichia, Bacillus, Pichia, Pseudomonas, Synechocystis,* or *Saccharomyces*.

8. A method according to claim 7, wherein the bacterial strain is a *Clostridium* species.

9. A method according to claim 8, wherein the *Clostridium* species is *Clostridium acetobutylicum, Clostridium beijerinckii, Clostridium saccharobutylicum, Clostridium puniceum, Clostridium saccharoperbutylacetonicum, Clostridium pasteuranium, Clostridium butylicum, Clostridium aurantibutyricum, Clostridium tetanomorphum, Clostridium thermocellum,* or *Clostridium thermosaccharolyticum*.

10. A method according to claim 1, wherein the salt is an inorganic salt.

11. A method according to claim 10, wherein the salt is selected from sodium chloride, potassium chloride, potassium phosphate, ammonium sulfate, calcium chloride, and calcium phosphate, or a mixture thereof.

12. A method for selecting a microbial strain that produces a bioproduct at an increased titer in comparison with a bioproduct producing parent strain, comprising culturing mutants of a bioproduct-producing microbial strain on solid growth medium or in liquid growth medium that comprises salt in an amount sufficient to inhibit growth of the bioproduct producing parent strain by at least about 99%, selecting microbial colonies that grow in the presence of said salt, and identifying said microbial strain that produces bioproduct at an increased titer by assessing the bioproduct titer of said colonies when grown in fermentation medium under conditions suitable for bioproduct production.

* * * * *